US009073950B2

(12) United States Patent
Kown acka et al.

(10) Patent No.: US 9,073,950 B2

(45) Date of Patent: Jul. 7, 2015

(54) HYDROSILYLATION REACTION CATALYSTS AND CURABLE COMPOSITIONS AND METHODS FOR THEIR PREPARATION AND USE

(71) Applicant: Dow Corning Corporation, Midland, MI (US)

(72) Inventors: Agnieszka Kownacka, Poznan (PL); Ireneusz Kownacki, Poznan (PL); Bogdan Marciniec, Swarzedz (PL); Binh Nguyen, Midland, MI (US); Avril Surgenor, Watterloo (BE); Richard Taylor, Sully (GB); Ming-Shin Tzou, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 14/343,581

(22) PCT Filed: Nov. 8, 2012

(86) PCT No.: PCT/US2012/064088

§ 371 (c)(1),
(2) Date: Mar. 7, 2014

(87) PCT Pub. No.: WO2013/081794

PCT Pub. Date: Jun. 6, 2013

(65) Prior Publication Data

US 2014/0296468 A1 Oct. 2, 2014

Related U.S. Application Data

(60) Provisional application No. 61/565,585, filed on Dec. 1, 2011.

(51) Int. Cl.

| | |
|---|---|
| ***C08G 77/08*** | (2006.01) |
| ***C07F 7/08*** | (2006.01) |
| ***B01J 31/22*** | (2006.01) |
| *B01J 31/02* | (2006.01) |
| *B01J 31/12* | (2006.01) |
| *B01J 37/34* | (2006.01) |

(52) U.S. Cl.

CPC ............ *C07F 7/0879* (2013.01); *B01J 31/0274* (2013.01); *B01J 31/124* (2013.01); *B01J 37/345* (2013.01); *B01J 31/2291* (2013.01); *B01J 2231/323* (2013.01); *B01J 2531/842* (2013.01); *C08G 77/08* (2013.01)

(58) Field of Classification Search

CPC .. B01J 31/2291; B01J 31/0274; B01J 31/124; B01J 37/345; C08G 77/08

See application file for complete search history.

(56) References Cited

U.S. PATENT DOCUMENTS

| | | | |
|---|---|---|---|
| 3,159,601 A | | 12/1964 | Ashby |
| 3,220,972 A | | 11/1965 | Lamoreaux |
| 3,296,291 A | | 1/1967 | Chalk et. al. |
| 3,351,648 A | * | 11/1967 | Weiss ........................... 548/404 |
| 3,419,593 A | | 12/1968 | Willing |
| 3,445,420 A | | 5/1969 | Kookootsedes et. al. |
| 3,516,946 A | | 6/1970 | Modic |
| 3,806,531 A | * | 4/1974 | von Gustorf et al. ......... 556/141 |
| 3,814,730 A | | 6/1974 | Karstedt |
| 3,989,667 A | | 11/1976 | Lee et al. |
| 3,989,668 A | | 11/1976 | Lee et al. |
| 4,087,585 A | | 5/1978 | Schulz |
| 4,284,751 A | | 8/1981 | Hutt et al. |
| 4,332,654 A | | 6/1982 | Yates |
| 4,766,176 A | | 8/1988 | Lee et al. |
| 4,784,879 A | | 11/1988 | Lee et al. |
| 4,900,772 A | | 2/1990 | Imanaka et al. |
| 5,017,654 A | | 5/1991 | Togashi et al. |
| 5,036,117 A | | 7/1991 | Chung et al. |
| 5,063,267 A | | 11/1991 | Hanneman et al. |
| 5,175,325 A | | 12/1992 | Brown et al. |
| 5,194,649 A | | 3/1993 | Okawa |
| 5,248,715 A | | 9/1993 | Gray et al. |
| 5,290,873 A | | 3/1994 | Noda et al. |
| 5,504,049 A | | 4/1996 | Crowther et al. |
| 5,580,925 A | | 12/1996 | Iwahara et al. |
| 5,744,507 A | | 4/1998 | Angell et al. |
| 6,169,142 B1 | | 1/2001 | Nakano et al. |

(Continued)

FOREIGN PATENT DOCUMENTS

| | | |
|---|---|---|
| EP | 0347895 A2 | 12/1989 |
| GB | 787175 | 12/1957 |

(Continued)

OTHER PUBLICATIONS

Akyuz, et. al., "Solid-State Vibrational Spectroscopy. Part V. An Infrared and Raman Spectroscopic of Metal(ii) Halide Pyridine Complexes", J.C.S. Dalton , 1976, pp. 1746-1749.

Archer, et. al., "Arene Coordination in Bis(imino)pyridine Iron Complexes: Identification of Catalyst Deactivation Pathways in Iron-Catalyzed Hydrogenation and Hydrosiliation" Organometallics, 2006, pp. 4269-4278, vol. 25.

Belger, et. al., "Aryl-aryl interactions as directing motifs in the stereodivergent iron-catalyzed hydrosilylation of internal alkynes", ChemComm, 2012, pp. 5419-5421, vol. 48.

(Continued)

*Primary Examiner* — Margaret Moore

(74) *Attorney, Agent, or Firm* — Catherine U. Brown

(57) ABSTRACT

A composition contains (A) a hydrosilylation reaction catalyst and (B) an aliphatically unsaturated compound having an average, per molecule, of one or more aliphatically unsaturated organic groups capable of undergoing hydrosilylation reaction. The composition is capable of reacting via hydrosilylation reaction to form a reaction product, such as a silane, a gum, a gel, a rubber, or a resin. Ingredient (A) contains an iron-organosilicon ligand complex that can be prepared by reacting an iron carbonyl compound and an organosilicon ligand.

17 Claims, No Drawings

(56) References Cited

U.S. PATENT DOCUMENTS

| | | | |
|---|---|---|---|
| 6,177,519 | B1 | 1/2001 | Chung et al. |
| 6,177,528 | B1 | 1/2001 | Lapointe et al. |
| 6,177,585 | B1 | 1/2001 | Chen et al. |
| 6,350,916 | B1 | 2/2002 | Guram et al. |
| 6,362,309 | B1 | 3/2002 | Lund et al. |
| 6,610,805 | B1 | 8/2003 | Guram et al. |
| 6,974,878 | B2 | 12/2005 | Guram et al. |
| 7,078,164 | B1 | 7/2006 | Diamond et al. |
| 7,229,943 | B2 | 6/2007 | Gibson et al. |
| 7,253,133 | B2 | 8/2007 | Sun et al. |
| 7,758,897 | B2 | 7/2010 | Roettger et al. |
| 7,858,706 | B2 | 12/2010 | Arriola et al. |
| 7,902,290 | B2 | 3/2011 | Nishiumi et al. |
| 8,053,529 | B2 | 11/2011 | Carnahan et al. |
| 8,101,251 | B2 | 1/2012 | Scott et al. |
| 8,236,915 | B2 * | 8/2012 | Delis et al. ...................... 528/14 |
| 8,372,927 | B2 | 2/2013 | Figueroa et al. |
| 8,440,312 | B2 | 5/2013 | Elahee |
| 8,461,283 | B2 | 6/2013 | Maliverney et al. |
| 8,481,640 | B2 | 7/2013 | Gough et al. |
| 8,497,331 | B2 | 7/2013 | Hillairet et al. |
| 8,592,545 | B2 | 11/2013 | Mackinnon et al. |
| 2002/0010291 | A1 | 1/2002 | Murphy |
| 2006/0258867 | A1 | 11/2006 | Gibson et al. |
| 2007/0224641 | A1 | 9/2007 | Campbell |
| 2008/0118734 | A1 | 5/2008 | Goodwin et al. |
| 2008/0300358 | A1 | 12/2008 | Cook et al. |
| 2010/0113260 | A1 | 5/2010 | Hagemeyer |
| 2010/0184883 | A1 | 7/2010 | Detemmerman et al. |
| 2011/0009573 | A1 * | 1/2011 | Delis et al. .................... 525/453 |
| 2011/0021684 | A1 | 1/2011 | Maliverney et al. |
| 2011/0178220 | A1 | 7/2011 | Davio et al. |
| 2012/0009366 | A1 | 1/2012 | Galbraith et al. |
| 2012/0130105 | A1 | 5/2012 | Lewis et al. |
| 2012/0130106 | A1 | 5/2012 | Chirik et al. |
| 2014/0249281 | A1 * | 9/2014 | Hedden et al. ................ 526/118 |

FOREIGN PATENT DOCUMENTS

| | | | |
|---|---|---|---|
| JP | 2005306994 | | 11/2005 |
| WO | 0032572 | A2 | 6/2000 |
| WO | 0119786 | A1 | 3/2001 |
| WO | 02058641 | A1 | 9/2002 |
| WO | 2010016416 | A2 | 2/2010 |
| WO | 2013158272 | A1 | 10/2013 |

OTHER PUBLICATIONS

Bhattacharya, et. al., "Iron Hydride Complexes Bearing Phosphinite-Based Pincer Ligands: Synthesis, Reactivity, and Catalytic Application in Hydrosilylation Reactions", Organometallics, 2011, pp. 4720-4729.

Bhattacharya, et. al., "Synthesis and Catalytic Applications of Iron Pincer Complexes", Inorganic Chemistry, Dec. 12, 2011, pp. 88-112, vol. 32.

Bianchini, et. al., "Simultaneous Polymerization and Schulz-Flory Oligomerization of Ethylene Made Possible by Activation with MAO of a C1-Symmetric [2,6-Bix(arylimino)pyridyl]iron Dichloride Precursor", Organometallics, 2004, pp. 6087-6089, vol. 23.

Boddien, et. al., "Iron-Catalyzed Hydrogen Production from Formic Acid", J. Am. Chem. Soc., 2010, pp. 8924-8934, vol. 132.

Boudier, et. al., "Novel Catalytic System for Ethylene Oligomerization: An Iron(III) Complex with an Anionic N,N,N Ligand", Organometallics, Mar. 3, 2011, pp. A-C.

Bowman, et. al., "Synthesis and Electronic Structure Determination of N-Alkyl-Substituted Bis(imino)pyridine Iron Imides Exhibiting Spin Crossover Behavior", J. Am. Chem. Soc., 2011, pp. 17353-17369, vol. 133.

Chirik, et. al., "Exploring Organometallics with P.J. Chirik's Work as Central Themes", Organometallics for Sustainability, 2010, pp. 1-11, Literature Seminar.

Chirik, Paul J., "Preface: Forum on Redox-Active Ligands", Inorganic Chemistry, 2011, pp. 9737-9740, vol. 50, Princeton, New Jersey, US.

Connelly, et. al., "Chemical Redox Agents for Organometallic Chemistry", Chem. Rev., 1996, pp. 877-910, vol. 96, Burlington, Vermont, US.

Field, et. al., "Iron(O) and Ruthenium(O) Complexes of Dinitrogen", Inorg. Chem., 2009, pp. 2246-2253, vol. 48, Scotland, United Kingdom.

Gibson, et. al., "Aluminum Alkyl-Mediated Route to Novel N,N,O-Chelates for Five-Coordinate Iron(II) Chloride Complexes: Synthesis, Structures, and Ethylene Polmerization Studies", Organometallics, 2007, pp. 5119-5123, vol. 26.

Hao, et. al., "A Cationic NCN Pincer Platinum(II) Aquo Complex with a Bis(imidazolinyl)phenyl Ligand: Studies toward its Synthesis and Asymmetric Friedel-Crafts Alkylation of Indoles with Nitroalkenes", Organometallics, 2011, pp. A-L, China.

Kakiuchi, et. al., "Completely Selective Synthesis of (E)-B-(triethylsilyl)styrenes by Fe3(CO)12-Catalyzed Reaction of Styrenes with Triethylsilane", J. Organometallic Chemistry, 1993, pp. 45-47, vol. 456.

Kamata, et. al., "Catalytic Hydrosilylation of Alkenes by Iron Complexes Containing Terpyridine Derivatives as Ancillary Ligands", Organometallics, Apr. 6, 2012, pp. A-D.

Lozan, et. al., "Coordination Compounds of Iron with Thiocarbazidediacetic and Semicarbazidediacetic Acids", Russian Journal of Coordination Chemistry, 1995, pp. 114-116, vol. 21, No. 2.

Marciniec, Bogdan, "Catalysis by transition metal complexes of alkene silylation-recent progress and mechanistic implications", Coordination Chemistry Reviews, 2005, pp. 2374-2390, vol. 249, Poznan, Poland.

Nakazawa, et. al., "Fe-H Complexes in Catalysis", Top Organomet. Chem., 2011, pp. 27-81, No. 33, Berlin, Heidelberg.

Naumov, et. al., "Selective Dehydrogenative Silylation-Hydrogenation Reaction of Divinyldisiloxane with Hydrosilane Catalyzed by an Iron Complex", J. Am. Chem. Soc., 2011, pp. A-D.

Pittman, et. al., "Photogeneration of Polymer-Anchored Catalytic Species From Iron Carbonyls", Fundamental Research in Homogeneous Catalysis, Jan. 1979, pp. 603-619, Plenum Press, NY, NY.

Putzien, et. al., "Functionalized polysilalkylene siloxanes (polycarbosiloxanes) by hydrosilylation-Catalysis and synthesis", Progress in Polymer Science, 2010, pp. 687-713, vol. 35, Germany.

Rosenheim, et. al., "Verbindungen des dreiwertigen Vanadiums", Zeitschrift fur Anorganische und Allggemeine Chemie, 1931, Band 201, pp. 162-174.

Russell, et. al., "Iron-Catalyzed Intermolecular Cycloaddition", J. Am. Chem. Soc., 2011, pp. 8858-8861, vol. 133.

* cited by examiner

HYDROSILYLATION REACTION CATALYSTS AND CURABLE COMPOSITIONS AND METHODS FOR THEIR PREPARATION AND USE

CROSS REFERENCE TO RELATED APPLICATIONS

This application is a U.S. national stage filing under 35 U.S.C. §371 of PCT Application No. PCT/U.S. Ser. No. 12/064,088 filed on 8 Nov. 2012, currently pending, which claims the benefit of U.S. Provisional Patent Application No. 61/565,585 filed 1 Dec. 2011 under 35 U.S.C. §119 (e). PCT Application No. PCT/U.S. Ser. No. 12/064,088 and U.S. Provisional Patent Application No. 61/565,585 are hereby incorporated by reference.

Catalysts for catalyzing hydrosilylation reaction are known in the art and are commercially available. Such conventional hydrosilylation catalysts can be a metal selected from platinum, rhodium, ruthenium, palladium, osmium, and iridium. Alternatively, the hydrosilylation catalyst may be a compound of such a metal, for example, chloroplatinic acid, chloroplatinic acid hexahydrate, platinum dichloride, and complexes of said compounds with low molecular weight organopolysiloxanes or platinum compounds microencapsulated in a matrix or core/shell type structure. Complexes of platinum with low molecular weight organopolysiloxanes include 1,3-diethenyl-1,1,3,3-tetramethyldisiloxane complexes with platinum. These complexes may be microencapsulated in a resin matrix. Alternatively, a hydrosilylation catalyst may comprise 1,3-diethenyl-1,1,3,3-tetramethyldisiloxane complex with platinum. Exemplary hydrosilylation catalysts are described in U.S. Pat. Nos. 3,159,601; 3,220,972; 3,296,291; 3,419,593; 3,516,946; 3,814,730; 3,989,668; 4,784,879; 5,036,117; and 5,175,325 and EP 0 347 895 B. Microencapsulated hydrosilylation catalysts and methods of preparing them are known in the art, as exemplified in U.S. Pat. Nos. 4,766,176 and 5,017,654.

These hydrosilylation catalysts suffer from the drawback of being extremely costly. Some of the metals in these hydrosilylation catalysts may also be difficult to obtain, and some of these hydrosilylation catalysts may be difficult to prepare. There is a need in industry to replace the conventional hydrosilylation catalysts described above with a less expensive and/or more readily available alternative. There is further a need to provide efficient catalysts, giving high yields, fast cure or good selectivity in the hydrosilylation reaction.

BRIEF SUMMARY OF THE INVENTION

A Fe-ligand complex and methods for its preparation are disclosed. A composition, which is capable of forming a reaction product via hydrosilylation reaction, comprises the Fe-ligand complex and an aliphatically unsaturated compound having an average, per molecule, of one or more aliphatically unsaturated organic groups capable of undergoing hydrosilylation reaction. When the aliphatically unsaturated compound lacks a silicon bonded hydrogen atom, then the composition further comprises an SiH functional compound having an average, per molecule, of one or more silicon bonded hydrogen atoms.

DETAILED DESCRIPTION OF THE INVENTION

All amounts, ratios, and percentages are by weight unless otherwise indicated. The articles 'a', 'an', and 'the' each refer to one or more, unless otherwise indicated by the context of specification. The disclosure of ranges includes the range itself and also anything subsumed therein, as well as endpoints. For example, disclosure of a range of 2.0 to 4.0 includes not only the range of 2.0 to 4.0, but also 2.1, 2.3, 3.4, 3.5, and 4.0 individually, as well as any other number subsumed in the range. Furthermore, disclosure of a range of, for example, 2.0 to 4.0 includes the subsets of, for example, 2.1 to 3.5, 2.3 to 3.4, 2.6 to 3.7, and 3.8 to 4.0, as well as any other subset subsumed in the range. Similarly, the disclosure of Markush groups includes the entire group and also any individual members and subgroups subsumed therein. For example, disclosure of the Markush group a hydrogen atom, an alkyl group, an aryl group, and an aralkyl group includes the member alkyl individually; the subgroup alkyl and aryl; and any other individual member and subgroup subsumed therein.

"Aralkyl" means an alkyl group having a pendant and/or terminal aryl group or an aryl group having a pendant alkyl group. Exemplary aralkyl groups include benzyl, phenylethyl, phenyl propyl, and phenyl butyl.

"Carbocycle" and "carbocyclic" each mean a hydrocarbon ring. Carbocycles may be monocyclic or alternatively may be fused, bridged, or spiro polycyclic rings. Monocyclic carbocycles may have 3 to 9 carbon atoms, alternatively 4 to 7 carbon atoms, and alternatively 5 to 6 carbon atoms. Polycyclic carbocycles may have 7 to 17 carbon atoms, alternatively 7 to 14 carbon atoms, and alternatively 9 to 10 carbon atoms. Carbocycles may be saturated or partially unsaturated.

"Cycloalkyl" means a saturated carbocycle. Cycloalkyl groups are exemplified by cyclobutyl, cyclopentyl, and cyclohexyl.

Abbreviations used herein are defined as follows. The abbreviation "cP" means centiPoise, and "cSt" means centiStokes. "DP" means the degree of polymerization of a polymer. "FTIR" means Fourier transform infrared spectroscopy. "GC" means gas chromatography. "GPC" means gel permeation chromatography. "Mn" means number average molecular weight. Mn may be measured using GPC. "Mw" means weight average molecular weight. "NMR" means nuclear magnetic resonance. "Pas" means Pascal seconds, and "ppm" means parts per million. "COD" means cyclooctadienyl. "Cp" means cyclopentyl. "Et" means ethyl. "Me" means methyl. "Ph" means phenyl. "Pr" means propyl and includes various structures such as iPr and nPr. "iPr" means isopropyl. "nPr" means normal propyl. "Bu" means butyl and includes various structures including nBu, sec-butyl, tBu, and iBu. "iBu" means isobutyl. "nBu" means normal butyl. "tBu" means tertiary-butyl. "AcAc" means acetyl acetonate. "2-EHA" means 2-ethylhexanoate. "OAc" means acetate. "Hex" means hexenyl. "Vi" means vinyl.

"M-unit" means a siloxane unit having formula $R_3SiO_{1/2}$, where each R independently represents a monovalent atom or organic group. "D-unit" means a siloxane unit having formula $R_2SiO_{2/2}$, where each R independently represents a monovalent atom or group. "T-unit" means a siloxane unit having formula $RSiO_{3/2}$, where each R independently represents a monovalent atom or group. "Qunit" means a siloxane unit having formula $SiO_{4/2}$.

"Non-functional" means that the ingredient does not have either an aliphatically unsaturated substituent or a silicon bonded hydrogen atom that participates in a hydrosilylation reaction.

"Free of" means that the composition contains a non-detectable amount of the ingredient, as compared to the same composition with the ingredient omitted. For example, the composition described herein may be free of platinum catalysts. "Free of platinum catalysts" means that the composition contains a non-detectable amount of a platinum catalyst capable of catalyzing a hydrosilylation reaction with the unsaturated groups on other ingredients in the composition, as compared to the same composition with the platinum catalyst omitted. The composition may be free of conventional metal catalysts. "Free of conventional metal catalysts" means that the composition contains a non-detectable amount of a the metal selected from Pt, Rh, Ru, Pd, Os, and Ir, or the compound of such a metal capable of catalyzing a hydrosilylation reaction with the unsaturated groups on other ingredients in the composition, as compared to the same composition with the conventional metal catalyst omitted. Alternatively, the composition described herein may be free of hydrosilylation reaction catalysts (i.e., free of any ingredient capable of catalyzing a hydrosilylation reaction of the aliphatically unsaturated groups on ingredient (B), described below, other than ingredient (A) described herein).

The composition, which has at least one ingredient capable of reacting by hydrosilylation reaction (composition), comprises:

(A) a Fe containing hydrosilylation reaction catalyst, and (B) an aliphatically unsaturated compound having an average, per molecule, of one or more aliphatically unsaturated organic groups capable of undergoing hydrosilylation reaction.

Without wishing to be bound by theory, it is thought that the Fe containing hydrosilylation reaction catalyst is characterizable as being effective for catalyzing the hydrosilylation reaction of the composition. The hydrosilylation reaction of the composition prepares a reaction product. The reaction product may have a form selected from the group consisting of a silane, a gum, a gel, a rubber, and a resin.

When ingredient (B) lacks a silicon bonded hydrogen atom, then the composition further comprises ingredient (C), an SiH functional compound having an average, per molecule, of one or more silicon bonded hydrogen atoms, which is distinct from ingredients (A) and (B).

The composition may optionally further comprise one or more additional ingredients, which are distinct from ingredient (A), ingredient (B), and ingredient (C) (if present) as described above. Suitable additional ingredients are exemplified by (D) a spacer; (E) an extender, a plasticizer, or a combination thereof; (F) a filler; (G) a filler treating agent; (H) a biocide; (I) a stabilizer, (J) a flame retardant; (K) a surface modifier; (L) a chain lengthener; (M) an endblocker; (N) a flux agent; (O) an anti-aging additive; (P) a pigment; (Q) an acid acceptor (R) a rheological additive; (S) a vehicle; (T) a surfactant; (U) a corrosion inhibitor; and a combination thereof.

Ingredient (A) comprises the Fe containing hydrosilylation reaction catalyst. The Fe containing hydrosilylation reaction catalyst comprises, or is prepared from, a Fe-ligand complex. The Fe-ligand complex can be prepared by reacting an iron carbonyl compound and a ligand. The iron carbonyl compound is distinct from the Fe-ligand complex. The iron carbonyl compound is distinct from a reaction product of the iron carbonyl compound and the ligand.

The iron carbonyl compound has general formula (i): $Fe_a—(CO)_b$, where subscript a is an integer with a value ranging from 1 to 3, and subscript b is an integer with a value ranging from 5 to 12 (i.e., b is 5 when a is 1, and b is 9 when a is 2, and b is 12 when a is 3). The carbonyl group can be displaced from Fe by the ligand to form the Fe-ligand complex. One or more carbonyl groups are displaced by a complexation reaction between the iron carbonyl compound and the ligand to form the Fe-ligand complex.

The iron carbonyl compound may be commercially available, such as Iron(0)pentacarbonyl of formula $Fe(CO)_5$ or diironnonacarbonyl of formula $Fe_2(CO)_9$, both of which are commercially available from Sigma-Aldrich, Inc. of St. Louis, Mo., U.S.A.

The ligand is an organosilicon compound that coordinates with Fe. The ligand has, per molecule, at least one atom of Si and at least one aliphatically unsaturated group, such as an alkene or an alkyne. The ligand may be an organosilicon diene, an organosilicon triene, an organosilicon tetraene, or an alkenyl-functional polyorganosiloxane.

The ligand comprises unit formula:

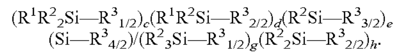

$$(R^1R^2_2Si—R^3_{1/2})_c(R^1R^2Si—R^3_{2/2})_d(R^2Si—R^3_{3/2})_e(Si—R^3_{4/2})_f(R^2_3Si—R^3_{1/2})_g(R^2_2Si—R^3_{2/2})_h.$$

Subscript c is 0 or more, subscript d is 0 or more, subscript e is 0 or more, subscript f is 0 or more, subscript g is 0 or more, and subscript h is 0 or more; with the proviso that (c+d+e+f) >0. A quantity (c+d+e+f+g+h) may be 1. Alternatively, the ligand may optionally contain small amounts of other units. Each $R^1$ is independently an alkynyl group such as ethynyl or propynyl; or an alkenyl group such as Vi, allyl, propenyl, butenyl, or Hex. Alternatively, each $R^1$ is an alkenyl group such as Vi. Each $R^2$ is independently an alkyl group, a cycloalkyl group, or an aryl group; alternatively an alkyl group or an aryl group. Alkyl groups are exemplified by Me, Et, Pr, and Bu; alternatively Me. Aryl groups for $R^2$ are exemplified by Ph, tolyl, xylyl, and benzyl; alternatively Ph. Each $R^3$ is an oxygen atom or an amino group of formula =NH. When $R^3$ is an oxygen atom and (d+e+f+h)>0, then the ligand is a polyorganosiloxane. When $R^3$ is an amino group and (d+e+f+h)>0, then the ligand is a polyorganosilazane.

Alternatively, the ligand may be a silane of formula (ii): $R^1_iSiR^2_{(4-i)}$, where $R^1$, $R^2$, and $R^3$ are as described above. Alternatively, each $R^1$ is Vi and each $R^2$ is Me. Subscript i is 2, 3, or 4. Alternatively, subscript i is 3.

Alternatively, the ligand may be a cyclic organosilicon compound of formula (iii): $(R^1R^2Si—R^3)_j$, where $R^1$, $R^2$, and $R^3$ are as described above. Alternatively, each $R^1$ is Vi, each $R^2$ is Me, and each $R^3$ is O. Subscript j is an integer with a value of at least 3, alternatively subscript j has a value ranging from 3 to 5, and alternatively subscript j is 4.

Alternatively, the ligand may be a linear organosilicon compound of formula (iv): $(R^1_kR^2_{2-k}Si—R^3)—(R^1R^2Si—R^3)_m(R^2_2Si—R^3_{2/2})_n—(SiR^1_kR^2_{2-k})$, where $R^1$, $R^2$, and $R^3$ are as described above. Alternatively, each $R^1$ is Vi, each $R^2$ is Me, and each $R^3$ is O. Subscript m is 1 or more, subscript n is 0 or more, and subscript k is 0 or 1. Alternatively, subscript m may range from 1 to 500. Alternatively, subscript n may range from 0 to 500. Alternatively, subscript m may have a value ranging from 1 to 100. Alternatively, subscript n may have a value ranging from 0 to 100. Alternatively, subscript k is 0.

Alternatively, the ligand may be a branched organosilicon compound of formula (v):

$(R^1R^2_2Si—R^3_{1/2})_3\ (R^2Si—R^3_{3/2})$, where $R^1$, $R^2$, and $R^3$ are as described above. Alternatively, each $R^1$ is Vi, each $R^2$ is Me, and each $R^3$ is O.

Ingredient (A) may be prepared by a method comprising reacting a ligand and an iron carbonyl compound, described above, thereby forming the catalytically active reaction product comprising the Fe-ligand complex. The method may optionally further comprise a step of dissolving either the iron carbonyl compound, or the ligand, or both, in a solvent before combining the Iron carbonyl compound and the ligand. Suitable solvents are exemplified by those described below for ingredient (S). Alternatively, the ligand may be dissolved in a solvent in a container, and the solvent may thereafter be removed before adding the Iron carbonyl compound to the container with the ligand. The amounts of ligand and iron carbonyl compound are selected such that the mole ratio of ligand to iron carbonyl compound (Ligand:Fe Ratio) may range from 100:1 to 1:10, alternatively 10:1 to 1:10, alternatively 2:1 to 1:2, and alternatively 1:1 to 2:1. Combining the iron carbonyl compound and the ligand may be performed by any convenient means, such as mixing them together in or shaking the container. Combining the iron carbonyl compound and the ligand may be performed in an inert atmosphere, such as by mixing under argon for 1 hour (h) to 30 hours.

Reacting the iron carbonyl compound and ligand may be performed by exposing the iron carbonyl compound and ligand prepared as described above to ultra-violet (UV) radiation at room temperature (RT) of 25° C. for a period of time. The complexation reaction conditions depend on various factors including the reactivities of the specific iron carbonyl compound and ligand selected and the Ligand:Fe Ratio, however, irradiation time may typically range from 1 minute (min) to 30 hours, alternatively 2 hours to 3 hours. The ligand and iron carbonyl compound may be combined and irradiated sequentially. Alternatively, the ligand and iron carbonyl compound may be combined and irradiated concurrently.

The method of preparing the catalytically active reaction product of ingredient (A) may optionally further comprise filtering and/or removing the solvent after irradiation. The solvent may be removed by any convenient means, such as drying under vacuum.

The method of preparing the catalytically active reaction product of ingredient (A) may optionally further comprise adding a vehicle after the reaction. Suitable vehicles are exemplified by those described below for ingredient (S). Alternatively, the method may optionally further comprise removing a reaction by-product and/or the vehicle, if the vehicle is present (e.g., used to facilitate combination of the iron carbonyl compound and the ligand before or during the complexation reaction By-products include, for example, H-A (where A is as defined above in general formula (i)) or any species resulting from reacting a substituent off the iron carbonyl compound when the ligand reacts with the iron carbonyl compound. By-products may be removed by any convenient means, such as stripping or distillation, with heating or under vacuum, or a combination thereof. The resulting isolated Fe-ligand complex may be used as the catalytically active reaction product of ingredient (A).

Alternatively, the reaction by-products are not removed before using the catalytically active reaction product as ingredient (A). For example, the ligand and iron carbonyl compound may be reacted as described above, with or without solvent removal, and the resulting reaction product (comprising the Fe-ligand complex and the reaction by-product and optionally a solvent or diluent) may be used as ingredient (A). Without wishing to be bound by theory, it is thought that a by-product may act as a hydrosilylation reaction catalyst, or as a co-catalyst or an activator, in addition to the Fe-ligand complex. Therefore, the reaction product may catalyze a hydrosilylation reaction. Alternatively, ingredient (A) may be formed in a molar excess amount of ingredient ii) the ligand. When the ligand is an aliphatically unsaturated polyorganosiloxane, and an excess amount is used in the method, then excess untreated ligand may serve as all, or a portion of, the aliphatically unsaturated compound described below as ingredient (B).

The composition may contain one single catalyst. Alternatively, the composition may comprise two or more catalysts described above as ingredient (A), where the two or more catalysts differ in at least one property such as selection of ligand, selection of iron carbonyl compound, Ligand:Metal Ratio, and definitions for group A in general formula (i). The composition may be free of platinum catalysts. Alternatively, the composition may be free of conventional metal catalysts. Alternatively, the composition may be free of any Fe compound that would catalyze the hydrosilylation reaction of the unsaturated groups on ingredient (B) other than the ingredient (A). Alternatively, the composition may be free of hydrosilylation reaction catalysts other than ingredient (A). Alternatively, the composition may be free of any ingredient that would catalyze the hydrosilylation reaction of the unsaturated groups on ingredient (B) other than ingredient (A).

Ingredient (A) is present in the composition in a catalytically effective amount. The exact amount depends on various factors including reactivity of ingredient (A), the type and amount of ingredient (B), and the type and amount of any additional ingredient, if present. However, the amount of ingredient (A) in the composition may range from 1 part per million (ppm) to 5%, alternatively 1 ppm to 2%, alternatively 0.1% to 2%, and alternatively 1 ppm to 1%, based on total weight of all ingredients in the composition.

Ingredient (B) is an aliphatically unsaturated compound having an average, per molecule, of one or more aliphatically unsaturated organic groups capable of undergoing hydrosilylation reaction. Alternatively, ingredient (B) may have an average of two or more aliphatically unsaturated organic groups per molecule. The aliphatically unsaturated organic groups may be alkenyl exemplified by, but not limited to, vinyl, allyl, propenyl, butenyl, and hexenyl. The unsaturated organic groups may be alkynyl groups exemplified by, but not limited to, ethynyl, propynyl, and butynyl.

Ingredient (B) of the composition may be an unsaturated hydrocarbon, where the unsaturated group is capable of reacting via hydrosilylation reaction. Ingredient (B) may be monomeric. For example, suitable aliphatically unsaturated organic compounds for ingredient (B) include, but are not limited to alkenes such as ethylene, propene, 1-butene, 2-butene, 1-pentene, 1-hexene, 1-heptene; halogenated alkenes, such as allyl chloride; diolefins such as divinylbenzene, butadiene, 1,5-hexadiene, and 1-buten-3-yne; cycloolefins such as cyclohexene and cycloheptene; and alkynes such as acetylene, propyne, and 1-hexyne.

Oxygen-containing aliphatically unsaturated compounds can also be used for ingredient (B), for example, where the unsaturation is ethylenic, such as vinylcyclohexyl epoxide, allyl glycidyl ether, methylvinyl ether, divinylether, phenylvinyl ether, monoallyl ether of ethylene glycol, allyl aldehyde, methylvinyl ketone, phenylvinyl ketone, acrylic acid, methacrylic acid, methyl acrylate, allyl acrylate, methyl methacrylate, allyl methacrylate, vinylacetic acid, vinyl acetate, and linolenic acid.

Heterocyclic compounds containing aliphatic unsaturation in the ring, such as dihydrofuran, and dihydropyran, are also suitable as ingredient (B). Unsaturated compounds containing nitrogen substituents such as acrylonitrile, N-vinylpyrrolidone, alkyl cyanide, nitroethylene are also suitable as ingredient (B).

Alternatively, ingredient (B) of the composition comprise a polymer. Ingredient (B) may comprise a base polymer having an average of one or more aliphatically unsaturated organic groups, capable of undergoing a hydrosilylation reaction, per molecule. Ingredient (B) may comprise a polymer (e.g., a homopolymer or an interpolymer, such as a copolymer or a terpolymer) of the various compounds described above, provided there is at least one aliphatic unsaturation capable of undergoing a hydrosilylation reaction. Examples include polymers derived from olefinic monomers having 2 to 20 carbon atoms and dienes having 4 to 20 carbon atoms; polymers of monoolefin, isomonoolefin and vinyl aromatic monomers, such as monoolefins having 2 to 20 carbon groups, isomonoolefins having 4 to 20 carbon groups, and vinyl aromatic monomers including styrene, para-alkylstyrene, para-methylstyrene. Alternatively, the polymers can be poly (dienes). Most polymers derived from dienes usually contain unsaturated ethylenic units on backbone or side-chains. Representative examples include polybutadiene, polyisoprene, polybutenylene, poly(alkyl-butenylene) where alkyl includes alkyl groups having 1 to 20 carbon atoms, poly(phenyl-butenylene), polypentenylene, natural rubber (a form of polyisoprene); and butyl rubber (copolymer of isobutylene and isoprene).

Alternatively, ingredient (B) may comprise a halogenated olefin polymer having aliphatic unsaturation. Representative examples of a halogenated olefin polymer having aliphatic unsaturation include polymers resulting from the bromination of a copolymer of isomonoolefin with para-methylstyrene to introduce benzylic halogen, halogenated polybutadienes, halogenated polyisobutylene, poly(2-chloro-1,3-butadiene), polychloroprene (85% trans), poly(1-chloro-1-butenylene) (Neoprene®), and chlorosulfonated polyethylene.

Alternatively, ingredient (B) may comprise polymers containing other compounds described above such as vinyl ether groups, acrylate groups, methyacrylate groups, and epoxy-functional groups.

Alternatively, ingredient (B) may comprise a silane having aliphatic unsaturation. Alternatively the silane may have a general formula of $R^{35}_{xx}SiR^{36}_{(4-xx)}$ where subscript xx is an integer from 1 to 4, alternatively 1 to 3, and alternatively 1. $R^{35}$ is an aliphatically unsaturaged organic group, and $R^{36}$ is selected from H, a halogen atom, and aa monovalent organic group.

Alternatively, ingredient (B) may comprise a silicon containing base polymer having a linear, branched, cyclic, or resinous structure having aliphatic unsaturation. Alternatively, the base polymer may have a linear and/or branched structure. Alternatively, the base polymer may have a resinous structure. The base polymer may be a homopolymer or a copolymer. Ingredient (B) may be one base polymer. Alternatively, ingredient (B) may comprise two or more base polymers differing in at least one of the following properties: structure, viscosity, average molecular weight, siloxane units, and sequence. The aliphatically unsaturated organic groups in the base polymer may be located at terminal, pendant, or both terminal and pendant positions.

The remaining silicon-bonded organic groups in the base polymer for ingredient (B) may be monovalent organic groups free of aliphatic unsaturation. Examples of monovalent hydrocarbon groups include, but are not limited to, alkyl such as methyl, ethyl, propyl, butyl, pentyl, hexyl, heptyl, octyl, decyl, dodecyl, undecyl, and octadecyl; cycloalkyl such as cyclopentyl and cyclohexyl; aryl such as phenyl, tolyl, xylyl, and naphthyl; alkaryl such as benzyl; and aralkyl such as 1-phenylethyl and 2-phenylethyl. Examples of monovalent halogenated hydrocarbon groups include, but are not limited to, chlorinated alkyl groups such as chloromethyl and chloropropyl groups; fluorinated alkyl groups such as fluoromethyl, 2-fluoropropyl, 3,3,3-trifluoropropyl, 4,4,4-trifluorobutyl, 4,4,4,3,3-pentafluorobutyl, 5,5,5,4,4,3,3-heptafluoropentyl, 6,6,6,5,5,4,4,3,3-nonafluorohexyl, and 8,8,8,7,7-pentafluorooctyl; chlorinated cycloalkyl groups such as 2,2-dichlorocyclopropyl, 2,3-dichlorocyclopentyl; and fluorinated cycloalkyl groups such as 2,2-difluorocyclopropyl, 2,3-difluorocyclobutyl, 3,4-difluorocyclohexyl, and 3,4-difluoro-5-methylcycloheptyl. Examples of other monovalent organic groups include, but are not limited to, hydrocarbon groups substituted with oxygen atoms such as glycidoxyalkyl, and hydrocarbon groups substituted with nitrogen atoms such as aminoalkyl and cyano-functional groups such as cyanoethyl and cyanopropyl.

Ingredient (B) may comprise a polydiorganosiloxane of $$R^1_2R^2SiO(R^1_2SiO)_a(R^1R^2SiO)_dSiR^1_2R^2, \quad \text{Formula (I)}$$

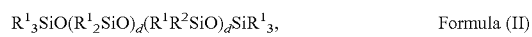

$$R^1_3SiO(R^1_2SiO)_d(R^1R^2SiO)_dSiR^1_3, \quad \text{Formula (II)}$$

or a combination thereof, e.g., a mixture of polydiorganosiloxanes of Formula (I) and Formula (II).

In formulae (I) and (II), each $R^1$ is independently a hydrogen atom or a monovalent organic group free of aliphatic unsaturation and each $R^2$ is independently an aliphatically unsaturated organic group, exemplified by those described above. Subscript a may be 0 or a positive number. Alternatively, subscript a has an average value of at least 2. Alternatively subscript a may have a value ranging from 2 to 2000. Subscript b may be 0 or a positive number. Alternatively, subscript b may have an average value ranging from 0 to 2000. Subscript c may be 0 or a positive number. Alternatively, subscript c may have an average value ranging from 0 to 2000. Subscript d has an average value of at least 2. Alternatively subscript d may have an average value ranging from 2 to 2000. Suitable monovalent organic groups for $R^1$ are as described above for ingredient (B). Alternatively, each $R^1$ is a monovalent hydrocarbon group exemplified by alkyl such as methyl and aryl such as phenyl. Each $R^2$ is independently an aliphatically unsaturated monovalent organic group as described above for ingredient (B). Alternatively, $R^2$ is exemplified by alkenyl groups such as vinyl, allyl, butenyl, and hexenyl; and alkynyl groups such as ethynyl and propynyl.

Ingredient (B) may comprise a polydiorganosiloxane such as i) dimethylvinylsiloxy-terminated polydimethylsiloxane,
ii) dimethylvinylsiloxy-terminated poly(dimethylsiloxane/methylvinylsiloxane),
iii) dimethylvinylsiloxy-terminated polymethylvinylsiloxane,
iv) trimethylsiloxy-terminated poly(dimethylsiloxane/methylvinylsiloxane),
v) trimethylsiloxy-terminated polymethylvinylsiloxane,
vi) dimethylvinylsiloxy-terminated poly(dimethylsiloxane/methylvinylsiloxane),
vii) dimethylvinylsiloxy-terminated poly(dimethylsiloxane/methylphenylsiloxane),
viii) dimethylvinylsiloxy-terminated poly(dimethylsiloxane/diphenylsiloxane),
ix) phenyl,methyl,vinyl-siloxy-terminated polydimethylsiloxane,
x) dimethylhexenylsiloxy-terminated polydimethylsiloxane,
xi) dimethylhexenylsiloxy-terminated poly(dimethylsiloxane/methylhexenylsiloxane),
xii) dimethylhexenylsiloxy-terminated polymethylhexenylsiloxane,
xiii) trimethylsiloxy-terminated poly(dimethylsiloxane/methylhexenylsiloxane),
xiv) trimethylsiloxy-terminated polymethylhexenylsiloxane
xv) dimethylhexenyl-siloxy terminated poly(dimethylsiloxane/methylhexenylsiloxane), xvi) dimethylvinylsiloxy-terminated poly(dimethylsiloxane/methylhexenylsiloxane)

xvii) a combination thereof.

Methods of preparing polydiorganosiloxane fluids suitable for use as ingredient (B), such as hydrolysis and condensation of the corresponding organohalosilanes or equilibration of cyclic polydiorganosiloxanes, are well known in the art.

In addition to, or instead of, the polydiorganosiloxane described above, ingredient (B) may further comprise a resin such as an MQ resin consisting essentially of $R^3{}_3SiO_{1/2}$ units and $SiO_{4/2}$ units, a TD resin consisting essentially of $R^3SiO_{3/2}$ units and $R^3{}_2SiO_{2/2}$ units, an MT resin consisting essentially of $R^3{}_3SiO_{1/2}$ units and $R^3SiO_{3/2}$ units, an MTD resin consisting essentially of $R^3{}_3SiO_{1/2}$ units, $R^3SiO_{3/2}$ units, and $R^3{}_2SiO_{2/2}$ units, or a combination thereof.

Each $R^3$ is a monovalent organic group exemplified by those described above for ingredient (B). Alternatively, the monovalent organic groups represented by $R^3$ may have 1 to 20 carbon atoms. Alternatively, examples of monovalent organic groups for $R^3$ include, but are not limited to, monovalent hydrocarbon groups and monovalent halogenated hydrocarbon groups.

The resin may contain an average of 3 to 30 mole percent of aliphatically unsaturated organic groups, alternatively 0.1 to 30 mole percent, alternatively 0.1 to 5 mole percent, alternatively 3 to 100 mole percent. The aliphatically unsaturated organic groups may be alkenyl groups, alkynyl groups, or a combination thereof. The mole percent of aliphatically unsaturated organic groups in the resin is the ratio of the number of moles of unsaturated group-containing siloxane units in the resin to the total number of moles of siloxane units in the resin, multiplied by 100.

Methods of preparing resins are well known in the art. For example, resin may be prepared by treating a resin copolymer produced by the silica hydrosol capping process of Daudt, et al. with at least an alkenyl-containing endblocking reagent. The method of Daudt et al., is disclosed in U.S. Pat. No. 2,676,182.

The method of Daudt, et al. involves reacting a silica hydrosol under acidic conditions with a hydrolyzable triorganosilane such as trimethylchlorosilane, a siloxane such as hexamethyldisiloxane, or mixtures thereof, and recovering a copolymer having M-units and Q-units. The resulting copolymers generally contain from 2 to 5 percent by weight of hydroxyl groups.

The resin, which typically contains less than 2% of silicon-bonded hydroxyl groups, may be prepared by reacting the product of Daudt, et al. with an unsaturated organic group-containing endblocking agent and an endblocking agent free of aliphatic unsaturation, in an amount sufficient to provide from 3 to 30 mole percent of unsaturated organic groups in the final product. Examples of endblocking agents include, but are not limited to, silazanes, siloxanes, and silanes. Suitable endblocking agents are known in the art and exemplified in U.S. Pat. Nos. 4,584,355; 4,591,622; and 4,585,836. A single endblocking agent or a mixture of such agents may be used to prepare the resin.

Alternatively, ingredient (B) may comprise a silicon containing base polymer other than the polyorganosiloxanes described above. For example, other compounds suitable for ingredient (B) include silazanes and/or polymeric materials containing silicon atoms joined together by hydrocarbyl groups such as alkylene or polyalkylene groups or arylene groups. The silicon-modified organic compounds useful as ingredient (B) include organic polymers having at least one silicon atom attached as a silane or a siloxane segment. The silicon-containing units can contain aliphatic unsaturation and can be attached at the terminal and/or pendant positions on the organic polymer chain or as a copolymer. Other representative silicon-modified organic polymers for ingredient (B) are exemplified by, but not limited to alkenylsiloxy-functional polymers such as vinylsiloxy-, allylsiloxy-, and hexenylsiloxy-organic polymers and siloxane-organic block copolymers. Examples of silane-modified organic polymers are silylated polymers derived from olefins, isomonoolefin, dienes, ethylene or propylene oxides, and vinyl aromatic monomers having 2 to 20 carbon atoms such as the silane-grafted copolymers of isomonoolefin and vinyl aromatic monomers.

Examples of silicon-modified organic polymers described by above include vinylsiloxy-terminated or hexenylsiloxy-terminated poly(dimethylsiloxane/hydrocarbyl) copolymers, vinylsiloxy-terminated or hexenylsiloxy-terminated poly(dimethylsiloxane/polyoxyalkylene) block copolymers, alkenyloxydimethylsiloxy-terminated polyisobutylene and alkenyloxydimethylsiloxy-terminated polydimethylsiloxane/polyisobutylene block copolymers. Examples of suitable compounds for ingredient (B) may be found, for example, in WO 2003/093369.

The amount of ingredient (B) in the composition depends on various factors including the desired form of the reaction product of the composition, the quantity and hydrosilylation reactivity of the aliphatically unsaturated groups of ingredient (B), the type and amount of ingredient (A), and the content of silicon bonded hydrogen atoms of, ingredient (B) and/or ingredient (C). However, the amount of ingredient (B) may range from 0.1% to 99.9% based on the weight of all ingredients in the composition.

Ingredient (C), which is optional in the composition as described previously, is a SiH functional compound, i.e., a compound having an average, per molecule, of one or more silicon bonded hydrogen atoms. Ingredient (C) may comprise a silane and/or an organohydrogensilicon compound. Alternatively, ingredient (C) may have an average, per molecule, of at least two silicon-bonded hydrogen atoms. The amount of ingredient (C) in the composition depends on various factors including the SiH content of ingredient (C), the unsaturated group content of ingredient (B), and the properties of the reaction product of the composition desired, however, the amount of ingredient (C) may be sufficient to provide a molar ratio of SiH groups in ingredient (C) to aliphatically unsaturated organic groups in ingredient (B) (commonly referred to as the SiH:Vi ratio) ranging from 0.3:1 to 10:1, alternatively 1:1 to 10:1. Ingredient (C) can have a monomeric or polymeric structure. When ingredient (C) has a polymeric structure, the polymeric structure may be linear, branched, cyclic, or resinous structure. When ingredient (C) is polymeric, then ingredient (C) can be a homopolymer or a copolymer. The silicon-bonded hydrogen atoms in ingredient (C) can be located at terminal, pendant, or at both terminal and pendant positions. Ingredient (C) may be one SiH functional compound. Alternatively, ingredient (C) may comprise a combination of two or more SiH functional compounds. Ingredient (C) may be two or more organohydrogenpolysiloxanes that differ in at least one of the following properties: structure, average molecular weight, viscosity, siloxane units, and sequence.

Ingredient (C) may comprise a silane of formula $R^4{}_eSiH_f$, where subscript e is 0, 1, 2, or 3; subscript f is 1, 2, 3, or 4, with the proviso that a sum of (e+f) is 4. Each $R^4$ is independently a halogen atom or a monovalent organic group. Suitable halogen atoms for $R^4$ are exemplified by chlorine, fluorine, bromine, and iodine; alternatively chlorine. Suitable monovalent organic groups for $R^4$ include, but are not limited to, monovalent hydrocarbon and monovalent halogenated hydrocarbon groups. Monovalent hydrocarbon groups include, but are not limited to, alkyl such as methyl, ethyl, propyl, butyl, pentyl, hexyl, heptyl, octyl, decyl, dodecyl, undecyl, and octadecyl; cycloalkyl such as cyclopentyl and cyclohexyl; aryl such as phenyl, tolyl, xylyl, and naphthyl; alkaryl such as benzyl; and aralkyl such as 1-phenylethyl and 2-phenylethyl. Examples of monovalent halogenated hydrocarbon groups include, but are not limited to, chlorinated alkyl groups such as chloromethyl and chloropropyl groups; fluorinated alkyl groups such as fluoromethyl, 2-fluoropropyl, 3,3,3-trifluoropropyl, 4,4,4-trifluorobutyl, 4,4,4,3,3-pentafluorobutyl, 5,5,5,4,4,3,3-heptafluoropentyl, 6,6,6,5,5,4,4,3,3-nonafluorohexyl, and 8,8,8,7,7-pentafluorooctyl; chlorinated cycloalkyl groups such as 2,2-dichlorocyclopropyl, 2,3-dichlorocyclopentyl; and fluorinated cycloalkyl groups such as 2,2-difluorocyclopropyl, 2,3-difluorocyclobutyl, 3,4-difluorocyclohexyl, and 3,4-difluoro-5-methylcycloheptyl. Examples of other monovalent organic groups include, but are not limited to, hydrocarbon groups substituted with oxygen atoms such as glycidoxyalkyl, and alkoxy groups such as methoxy, ethoxy, propoxy, and butoxy; and hydrocarbon groups substituted with nitrogen atoms such as aminoalkyl and cyano-functional groups such as cyanoethyl and cyanopropyl. Examples of suitable silanes for ingredient (C) are exemplified by trichlorosilane ($HSiCl_3$), $Me_2HSiCl$, or $MeHSROMe)_2$.

Alternatively, the organohydrogensilicon compound of ingredient (C) may comprise a polyorganohydrogensiloxane comprising siloxane units including, but not limited to, $HR^5_2SiO_{1/2}$, $R^5_3SiO_{1/2}$, $HR^5SiO_{2/2}$, $R^5_2SiO_{2/2}$, $R^5SiO_{3/2}$, $HSiO_{3/2}$, and $SiO_{4/2}$ units. In the preceding formulae, each $R^5$ is independently selected from the monovalent organic groups free of aliphatic unsaturation described above.

Ingredient (C) may comprise a polyorganohydrogensiloxane of

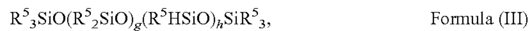

$R^5_3SiO(R^5_2SiO)_g(R^5HSiO)_hSiR^5_3$, Formula (III)

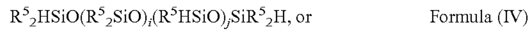

$R^5_2HSiO(R^5_2SiO)_i(R^5HSiO)_jSiR^5_2H$, or Formula (IV)

a combination thereof.

In formulae (III) and (IV) above, subscript g has an average value ranging from 0 to 2000, subscript h has an average value ranging from 2 to 2000, subscript i has an average value ranging from 0 to 2000, and subscript j has an average value ranging from 0 to 2000. Each $R^5$ is independently a monovalent organic group, as described above.

Polyorganohydrogensiloxanes for ingredient (C) are exemplified by:

a) dimethylhydrogensiloxy-terminated polydimethylsiloxane, b) dimethylhydrogensiloxy-terminated poly(dimethylsiloxane/m ethylhydrogensiloxane), c) dimethylhydrogensiloxy-terminated polymethylhydrogensiloxane, d) trimethylsiloxy-terminated poly(dimethylsiloxane/methylhydrogensiloxane), e) trimethylsiloxy-terminated polymethylhydrogensiloxane, f) a resin consisting essentially of $H(CH_3)_2SiO_{1/2}$ units and $SiO_{4/2}$ units, and g) a combination thereof.

Methods of preparing linear, branched, and cyclic organohydrogenpolysiloxanes suitable for use as ingredient (C), such as hydrolysis and condensation of organohalosilanes, are well known in the art. Methods of preparing organohydrogenpolysiloxane resins suitable for use as ingredient (C) are also well known as exemplified in U.S. Pat. Nos. 5,310,843; 4,370,358; and 4,707,531.

Alternatively, the organohydrogensilicon compound of ingredient (C) may comprise a compound of formula (V):

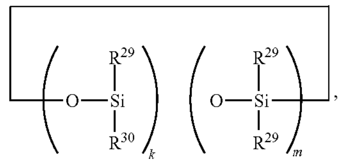

where each $R^{29}$ is independently selected from a hydrogen atom and a monovalent hydrocarbon group comprising 1 to 20 carbon atoms which is free from aliphatic unsaturation, subscript k is an integer with a value ranging from 1 to 18, subscript m is an integer with a value ranging from 2 to 19, k+m is an integer with a value ranging from 3 to 20, each $R^{30}$ is a functional group independently selected from a halogen atom, an ether group, an alkoxy group, an alkoxyether group, an acyl group, an epoxy group, an amino group, a silyl group, or a —Z—$R^{31}$ group, where each Z is independently selected from an oxygen atom and a divalent hydrocarbon group comprising 2 to 20 carbon atoms, each $R^{31}$ group is independently selected from $—BR^{29}_uR^{32}_{2-u}$, $—SiR^{29}_vR^{32}_{3-v}$, or a group described by formula (VI):

$$(R^{32}_{3-n}R^{29}_nSiO_{1/2})_w(R^{32}_{2-o}R^{29}_oSiO_{2/2})_x(R^{32}_{1-p}R^{29}_pSiO_{3/2})_y(SiO_{4/2})_z(CR^{29}_qR^{32}_{1-q})_{aa}(CR^{29}_rR^{32}_{2-r})_{bb}(O(CR^{29}_sR^{32}_{2-s})_{cc}(CR^{29}_tR^{32}_{3-t})_{dd}$$

where B refers to boron, each $R^{29}$ is as described above, the sum of w+x+y+z+aa+bb+cc+dd is at least 2, subscript n is an integer with a value ranging from 0 to 3, subscript o is an integer with a value ranging from 0 to 2, subscript p is an integer with a value ranging from 0 to 1, subscript q is an integer with a value ranging from 0 to 1, subscript r is an integer with a value ranging from 0 to 2, subscript s is an integer with a value ranging from 0 to 2, subscript t is an integer with a value ranging from 0 to 3, subscript u is an integer with a value ranging from 0 to 2, subscript v is an integer with a value ranging from 0 to 3, each $R^{32}$ is a functional group independently selected from a halogen atom, an ether group, an alkoxy group, an alkoxyether group, an acyl group, an epoxy group, an amino group, a silyl group, or a Z-G group, where Z is as described above, each G is a cyclosiloxane described by formula (VII):

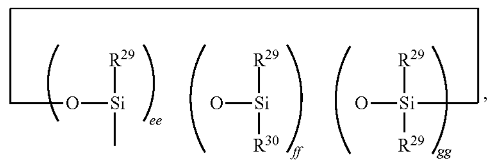

where $R^{29}$ and $R^{30}$ are as described above, subscript ee is 1, subscript ff is an integer with a value ranging from 0 to 18, subscript gg is an integer with a value ranging from 0 to 18, ff+gg is an integer with a value ranging from 2 to 20, provided in formula (VII) that one of the $R^{32}$ groups is replaced by the Z group bonding the $R^{31}$ group to the cyclosiloxane of formula (VII), and provided further if aa+bb+cc+dd>0 then w+x+y+z>0.

Such organohydrogensilicon compounds are commercially available and include, SYL-OFF® SL2 CROSSLINKER and SYL-OFF® SL12 CROSSLINKER, both of which are commercially available from Dow Corning Corporation of Midland, Mich., U.S.A. The organohydrogensilicon compounds described above and methods for their preparation are exemplified in WO2003/093349 and WO2003/093369. An exemplary organohydrogensilicon compound may have the general formula:

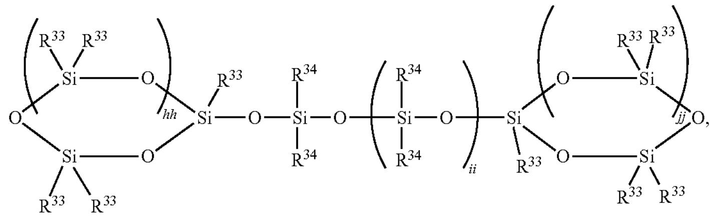

where each $R^{33}$ is independently selected from a hydrogen atom and a monovalent organic group; each $R^{34}$ is independently selected from a hydrogen atom, a monovalent organic group, and a group of formula

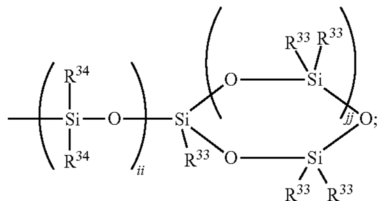

subscript hh is an integer with a value of at least 1; subscript jj is an integer with a value of at least 1; and subscript ii is an integer with a minimum value of 0. In the general formula, at least one instance of $R^{33}$ is a hydrogen atom. Suitable monovalent organic groups for $R^{33}$ and/or $R^{34}$ are exemplified by those groups described above for $R^{29}$.

The exact amount of ingredient (C) in the composition depends on various factors including reactivity of ingredient (A), the type and amount of ingredient (B), whether ingredient (B) contains a silicon bonded hydrogen atom, and the type and amount of any additional ingredient (other than ingredient (C)), if present. However, the amount of ingredient (C) in the composition may range from 0% to 25%, alternatively 0.1% to 15%, and alternatively 1% to 5%, based on total weight of all ingredients in the composition.

Ingredient (D) Spacer

Ingredient (D) is a spacer, e.g., that can be used to keep two substrates a certain distance apart from one another when a composition containing the spacer is interposed between the substrates. Spacers can comprise organic particles, inorganic particles, or a combination thereof. Spacers can be thermally conductive, electrically conductive, or both. Spacers can have a desired particle size, for example, particle size may range from 25 micrometers to 125 micrometers. Spacers can comprise monodisperse beads, such as glass or polymer (e.g., polystyrene) beads. Spacers can comprise thermally conductive fillers such as alumina, aluminum nitride, atomized metal powders, boron nitride, copper, and silver. The amount of ingredient (D) depends on various factors including the particle size distribution, pressure to be applied during use of the composition or the cured product prepared therefrom, temperature during use, and desired thickness of the composition or the cured product prepared therefrom. However, the composition may contain an amount of ingredient (D) ranging from 0.05% to 2%, alternatively 0.1% to 1%.

Ingredient (E) Extender

Ingredient (E) is an extender and/or a plasticizer. An extender comprising a non-functional polyorganosiloxane may be used in the composition. For example, the non-functional polyorganosiloxane may comprise difunctional units of the formula $R^6{}_2SiO_{2/2}$ and terminal units of the formula $R^7{}_3SiR^{28-}$, where each $R^6$ and each $R^7$ are independently a monovalent organic group such as a monovalent hydrocarbon group exemplified by alkyl such as methyl, ethyl, propyl, and butyl; alkenyl such as vinyl, allyl, and hexenyl; aryl such as phenyl, tolyl, xylyl, and naphthyl; and aralkyl groups such as phenylethyl; and $R^{28}$ is an oxygen atom or a divalent group linking the silicon atom of the terminal unit with another silicon atom. The divalent linking group for $R^{28}$ may be a divalent organic group, a silicone organic group, or a combination of a divalent hydrocarbon group and a divalent siloxane group. Alternatively, each $R^{28}$ may be independently selected from an oxygen atom and a divalent hydrocarbon group. Alternatively, each $R^{28}$ may be an oxygen atom. Alternatively, each $R^{28}$ may be a divalent hydrocarbon group exemplified by an alkylene group such as ethylene, propylene, butylene, or hexylene; an arylene group such as phenylene, or an alkylarylene group such as:

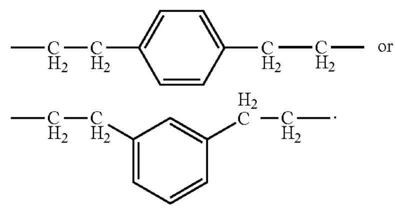

Alternatively, an instance of $R^{28}$ may be an oxygen atom while a different instance of $R^{28}$ is a divalent hydrocarbon group. Non-functional polyorganosiloxanes are known in the art and are commercially available. Suitable non-functional polyorganosiloxanes are exemplified by, but not limited to, polydimethylsiloxanes. Such polydimethylsiloxanes include DOW CORNING® 200 Fluids, which are commercially available from Dow Corning Corporation of Midland, Mich., U.S.A. and may have viscosity ranging from 50 cSt to 100,000 cSt, alternatively 50 cSt to 50,000 cSt, and alternatively 12,500 cSt to 60,000 cSt.

An organic plasticizer may be used in addition to, or instead of, the non-functional polyorganosiloxane extender described above. Organic plasticizers are known in the art and are commercially available. The organic plasticizer may comprise a phthalate, a carboxylate, a carboxylic acid ester, an adipate or a combination thereof. The organic plasticizer may be selected from the group consisting of: bis(2-ethylhexyl) terephthalate; bis(2-ethylhexyl)-1,4-benzenedicarboxylate; 2-ethylhexyl methyl-1,4-benzenedicarboxylate; 1,2 cyclohexanedicarboxylic acid, dinonyl ester, branched and linear; bis(2-propylheptyl) phthalate; diisononyl adipate; and a combination thereof.

The organic plasticizer may have an average, per molecule, of at least one group of formula

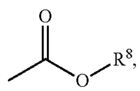

where $R^8$ represents a hydrogen atom or a monovalent organic group. Alternatively, $R^8$ may represent a branched or linear monovalent hydrocarbon group. The monovalent organic group may be a branched or linear monovalent hydrocarbon group such as an alkyl group of 4 to 15 carbon atoms, alternatively 9 to 12 carbon atoms. Suitable plasticizers may be selected from the group consisting of adipates, carboxylates, phthalates, and a combination thereof.

Alternatively, the organic plasticizer may have an average, per molecule, of at least two groups of the formula above bonded to carbon atoms in a cyclic hydrocarbon. The organic plasticizer may have general formula:

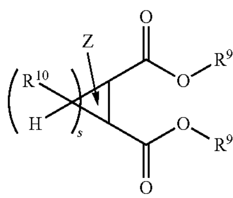

In this formula, group Z represents a cyclic hydrocarbon group having 3 or more carbon atoms, alternatively 3 to 15 carbon atoms. Subscript k may have a value ranging from 1 to 12. Group Z may be saturated or aromatic. Each $R^{10}$ is independently a hydrogen atom or a branched or linear monovalent organic group. The monovalent organic group for $R^9$ may be an alkyl group such as methyl, ethyl, or butyl. Alternatively, the monovalent organic group for $R^{10}$ may be an ester functional group. Each $R^9$ is independently a branched or linear monovalent hydrocarbon group, such as an alkyl group of 4 to 15 carbon atoms.

Suitable organic plasticizers are known in the art and are commercially available. The plasticizer may comprise a phthalate, such as: a dialkyl phthalate such as dibutyl phthalate (Eastman™ DBP Plasticizer), diheptyl phthalate, di(2-ethylhexyl) phthalate, or diisodecyl phthalate (DIDP), bis(2-propylheptyl) phthalate (BASF Palatinol® DPHP), di(2-ethylhexyl) phthalate (Eastman™ DOP Plasticizer), dimethyl phthalate (Eastman™ DMP Plasticizer); diethyl phthalate (Eastman™ DMP Plasticizer); butyl benzyl phthalate, and bis(2-ethylhexyl) terephthalate (Eastman™ 425 Plasticizer); a dicarboxylate such as Benzyl, C7-C9 linear and branched alkyl esters, 1,2, benzene dicarboxylic acid (Ferro SANTICIZER® 261A), 1,2,4-benzenetricarboxylic acid (BASF Palatinol® TOTM-I), bis(2-ethylhexyl)-1,4-benzenedicarboxylate (Eastman™ 168 Plasticizer); 2-ethylhexyl methyl-1,4-benzenedicarboxylate; 1,2 cyclohexanedicarboxylic acid, dinonyl ester, branched and linear (BASF Hexamoll *DINCH); diisononyl adipate; trimellitates such as trioctyl trimellitate (Eastman™ TO™ Plasticizer); triethylene glycol bis(2-ethylhexanoate) (Eastman™ TEG-EH Plasticizer); triacetin (Eastman™ Triacetin); nonaromatic dibasic acid esters such as dioctyl adipate, bis(2-ethylhexyl) adipate (Eastman™ DOA Plasticizer and Eastman™ DOA Plasticizer, Kosher), di-2-ethylhexyladipate (BASF Plastomoll® DOA), dioctyl sebacate, dibutyl sebacate and diisodecyl succinate; aliphatic esters such as butyl oleate and methyl acetyl recinolate; phosphates such as tricresyl phosphate and tributyl phosphate; chlorinated paraffins; hydrocarbon oils such as alkyldiphenyls and partially hydrogenated terphenyls; process oils; epoxy plasticizers such as epoxidized soybean oil and benzyl epoxystearate; tris(2-ethylhexyl) ester; a fatty acid ester; and a combination thereof. Examples of other suitable plasticizers and their commercial sources include BASF Palamoll® 652 and Eastman 168 Xtreme™ Plasticizer.

Alternatively, a polymer plasticizer can be used. Examples of the polymer plasticizer include alkenyl polymers obtained by polymerizing vinyl or allyl monomers by means of various methods; polyalkylene glycol esters such as diethylene glycol dibenzoate, triethylene glycol dibenzoate and pentaerythritol ester; polyester plasticizers obtained from dibasic acids such as sebacic acid, adipic acid, azelaic acid and phthalic acid and dihydric alcohols such as ethylene glycol, diethylene glycol, triethylene glycol, propylene glycol and dipropylene glycol; polyethers including polyether polyols each having a molecular weight of not less than 500 such as polyethylene glycol, polypropylene glycol and polytetramethylene glycol, polystyrenes such as polystyrene and poly-alpha-methylstyrene; and polybutadiene, polybutene, polyisobutylene, butadiene acrylonitrile, and polychloroprene.

The polyorganosiloxane extenders and organic plasticizers described above for ingredient (E) may be used either each alone or in combinations of two or more thereof. A low molecular weight organic plasticizer and a higher molecular weight polymer plasticizer may be used in combination. The exact amount of ingredient (E) used in the composition will depend on various factors including the desired end use of the composition and the cured product thereof. However, the amount of ingredient (E) may range from 0.1% to 10 based on the combined weights of all ingredients in the composition.

Ingredient (F) is a filler. The filler may comprise a reinforcing filler, an extending filler, a conductive filler, or a combination thereof. For example, the composition may optionally further comprise ingredient (f1), a reinforcing filler, which when present may be added in an amount ranging from 0.1% to 95%, alternatively 1% to 60%, based on the weight of the composition. The exact amount of ingredient (f1) depends on various factors including the form of the reaction product of the composition (e.g., gel or rubber) and whether any other fillers are added. Examples of suitable reinforcing fillers include chopped fiber such as chopped KEVLAR®, and/or reinforcing silica fillers such as fume silica, silica aerogel, silica xerogel, and precipitated silica. Fumed silicas are known in the art and commercially available; e.g., fumed silica sold under the name CAB-O-SIL by Cabot Corporation of Massachusetts, U.S.A.

The composition may optionally further comprise ingredient (f2) an extending filler in an amount ranging from 0.1% to 95%, alternatively 1% to 60%, and alternatively 1 to 20%, based on the weight of the composition. Examples of extending fillers include crushed quartz, aluminum oxide, magnesium oxide, calcium carbonate such as precipitated calcium carbonate, zinc oxide, talc, diatomaceous earth, iron oxide, clays, mica, titanium dioxide, zirconia, sand, carbon black, graphite, or a combination thereof. Extending fillers are known in the art and commercially available; such as a ground silica sold under the name MIN-U-SIL by U.S. Silica of Berkeley Springs, W. Va. Suitable precipitated calcium carbonates included Winnofil® SPM from Solvay and Ultrapflex® and Ultrapflex® 100 from SMI.

The composition may optionally further comprise ingredient (f3) a conductive filler. Ingredient (F) may be both thermally conductive and electrically conductive. Alternatively, ingredient (F) may be thermally conductive and electrically insulating. Ingredient (F) may be selected from the group consisting of aluminum nitride, aluminum oxide, aluminum trihydrate, barium titanate, beryllium oxide, boron nitride, carbon fibers, diamond, graphite, magnesium hydroxide, magnesium oxide, metal particulate, onyx, silicon carbide, tungsten carbide, zinc oxide, and a combination thereof. Ingredient (F) may comprise a metallic filler, an inorganic filler, a meltable filler, or a combination thereof. Metallic fillers include particles of metals and particles of metals having layers on the surfaces of the particles. These layers may be, for example, metal nitride layers or metal oxide layers on the surfaces of the particles. Suitable metallic fillers are exemplified by particles of metals selected from the group consisting of aluminum, copper, gold, nickel, silver, and combinations thereof, and alternatively aluminum. Suitable metallic fillers are further exemplified by particles of the metals listed above having layers on their surfaces selected from the group consisting of aluminum nitride, aluminum oxide, copper oxide, nickel oxide, silver oxide, and combinations thereof. For example, the metallic filler may comprise aluminum particles having aluminum oxide layers on their surfaces.

Inorganic conductive fillers are exemplified by onyx; aluminum trihydrate, metal oxides such as aluminum oxide, beryllium oxide, magnesium oxide, and zinc oxide; nitrides such as aluminum nitride and boron nitride; carbides such as silicon carbide and tungsten carbide; and combinations thereof. Alternatively, inorganic conductive fillers are exemplified by aluminum oxide, zinc oxide, and combinations thereof. Meltable fillers may comprise Bi, Ga, In, Sn, or an alloy thereof. The meltable filler may optionally further comprise Ag, Au, Cd, Cu, Pb, Sb, Zn, or a combination thereof. Examples of suitable meltable fillers include Ga, In—Bi—Sn alloys, Sn—In—Zn alloys, Sn—In—Ag alloys, Sn—Ag—Bi alloys, Sn—Bi—Cu—Ag alloys, Sn—Ag—Cu—Sb alloys, Sn—Ag—Cu alloys, Sn—Ag alloys, Sn—Ag—Cu—Zn alloys, and combinations thereof. The meltable filler may have a melting point ranging from 50° C. to 250° C., alternatively 150° C. to 225° C. The meltable filler may be a eutectic alloy, a non-eutectic alloy, or a pure metal. Meltable fillers are commercially available.

For example, meltable fillers may be obtained from Indium Corporation of America, Utica, N.Y., U.S.A.; Arconium, Providence, R.I., U.S.A.; and AIM Solder, Cranston, R.I., U.S.A. Aluminum fillers are commercially available, for example, from Toyal America, Inc. of Naperville, Ill., U.S.A. and Valimet Inc., of Stockton, Calif., U.S.A. Silver filler is commercially available from Metalor Technologies U.S.A. Corp. of Attleboro, Mass., U.S.A.

Thermally conductive fillers are known in the art and commercially available. For example, CB-A20S and Al-43-Me are aluminum oxide fillers of differing particle sizes commercially available from Showa-Denko, and AA-04, AA-2, and AA18 are aluminum oxide fillers commercially available from Sumitomo Chemical Company. Zinc oxides, such as zinc oxides having trademarks KADOX® and XX®, are commercially available from Zinc Corporation of America of Monaca, Pa., U.S.A.

The shape of the filler particles is not specifically restricted, however, rounded or spherical particles may prevent viscosity increase to an undesirable level upon high loading of the filler in the composition.

Ingredient (F) may be a single filler or a combination of two or more fillers that differ in at least one property such as particle shape, average particle size, particle size distribution, and type of filler. For example, it may be desirable to use a combination of fillers, such as a first filler having a larger average particle size and a second filler having a smaller average particle size. Use of a first filler having a larger average particle size and a second filler having a smaller average particle size than the first filler may improve packing efficiency and/or may reduce viscosity of the composition as compared to a composition without such a combination of fillers.

The average particle size of the filler will depend on various factors including the type of the filler selected for ingredient (F) and the exact amount added to the composition, as well as the end use for the reaction product of the composition. However, the filler may have an average particle size ranging from 0.1 micrometer to 80 micrometers, alternatively 0.1 micrometer to 50 micrometers, and alternatively 0.1 micrometer to 10 micrometers.

The amount of ingredient (F) in the composition depends on various factors including the end use selected for the composition and the reaction product of the composition, the type and amount of ingredient (B), and the type and amount of the filler selected for ingredient (F). However, the amount of ingredient (F) may range from 0 vol to 80 vol %, alternatively 50 vol % to 75 vol %, and alternatively 30% to 80%, by volume of the composition. Without wishing to be bound by theory, it is thought that when the amount of filler is greater than 80 vol %, the composition may react to form a reaction product with insufficient dimensional integrity for some applications.

The composition may optionally further comprise ingredient (G) a treating agent. The amount of ingredient (G) will vary depending on factors such as the type of treating agent selected and the type and amount of particulates (such as ingredients (F) and/or (D)) to be treated, and whether the particulates are treated before being added to the composition, or whether the particulates are treated in situ. However, ingredient (G) may be used in an amount ranging from 0.01% to 20%, alternatively 0.1% to 15%, and alternatively 0.5% to 5%, based on the weight of all ingredients in the composition. Particulates, such as the filler, the physical drying agent, certain flame retardants, and/or certain pigments, when present, may optionally be surface treated with ingredient (G). Particulates may be treated with ingredient (G) before being added to the composition, or in situ. Ingredient (G) may comprise an alkoxysilane, an alkoxy-functional oligosiloxane, a cyclic polyorganosiloxane, a hydroxyl-functional oligosiloxane such as a dimethyl siloxane or methyl phenyl siloxane, or a fatty acid. Examples of fatty acids include stearates such as calcium stearate.

Some representative organosilicon filler treating agents that can be used as ingredient (G) include compositions normally used to treat silica fillers such as organochlorosilanes, organosiloxanes, organodisilazanes such as hexaalkyl disilazane, and organoalkoxysilanes such as $C_6H_{13}Si(OCH_3)_3$, $C_8H_{17}Si(OC_2H_5)_3$, $C_{10}H_{21}Si(OCH_3)_3$, $C_{12}H_{25}Si(OCH_3)_3$, $C_{14}H_{29}Si(OC_2H_5)_3$, and $C_6H_5CH_2CH_2Si(OCH_3)_3$. Other treating agents that can be used include alkylthiols, fatty acids, titanates, titanate coupling agents, zirconate coupling agents, and combinations thereof.

Alternatively, ingredient (G) may comprise an alkoxysilane having the formula: $R^{11}_{m}Si(OR^{12})_{(4-m)}$, where subscript m may have a value ranging from 1 to 3, alternatively subscript m is 3. Each $R^{11}$ is independently a monovalent organic group, such as a monovalent hydrocarbon group of 1 to 50 carbon atoms, alternatively 8 to 30 carbon atoms, alternatively 8 to 18 carbon atoms. $R^{11}$ is exemplified by alkyl groups such as hexyl, octyl, dodecyl, tetradecyl, hexadecyl, and octadecyl; and aromatic groups such as benzyl and phenylethyl. $R^{11}$ may be saturated or unsaturated, and branched or unbranched. Alternatively, $R^{11}$ may be saturated and unbranched.

Each $R^{12}$ is independently a saturated hydrocarbon group of 1 to 4 carbon atoms, alternatively 1 to 2 carbon atoms. Alkoxysilanes suitable for use as ingredient (G) are exemplified by hexyltrimethoxysilane, octyltriethoxysilane, decyltrimethoxysilane, dodecyltrimethoxysilane, tetradecyltrimethoxysilane, phenylethyltrimethoxysilane, octadecyltrimethoxysilane, octadecyltriethoxysilane, and combinations thereof.

Alkoxy-functional oligosiloxanes may also be used as treating agents. For example, suitable alkoxy-functional oligosiloxanes include those of the formula (V): $(R^{13}O)_{n}Si(OSiR^{14}_{2}R^{15})_{(4-n)}$. In this formula, subscript n is 1, 2 or 3, alternatively subscript n is 3. Each $R^{13}$ may be an alkyl group. Each $R^{14}$ may be an unsaturated monovalent hydrocarbon group of 1 to 10 carbon atoms. Each $R^{15}$ may be an unsaturated monovalent hydrocarbon group having at least 10 carbon atoms.

Certain particulates, such as metal fillers may be treated with alkylthiols such as octadecyl mercaptan; fatty acids such as oleic acid and stearic acid; and a combination thereof.

Treatment agents for alumina or passivated aluminum nitride may include alkoxysilyl functional alkylmethyl polysiloxanes (e.g., partial hydrolysis condensate of $R^{16}_{o}R^{17}_{p}Si(OR^{18})_{(4-o-p)}$ or cohydrolysis condensates or mixtures), or similar materials where the hydrolyzable group may comprise silazane, acyloxy or oximo. In all of these, a group tethered to Si, such as $R^{16}$ in the formula above, is a long chain unsaturated monovalent hydrocarbon or monovalent aromatic-functional hydrocarbon. Each $R^{17}$ is independently a monovalent hydrocarbon group, and each $R^{18}$ is independently a monovalent hydrocarbon group of 1 to 4 carbon atoms. In the formula above, subscript o is 1, 2, or 3 and subscript p is 0, 1, or 2, with the proviso that a sum (o+p) is 1, 2, or 3.

Other treating agents include alkenyl functional polyorganosiloxanes. Suitable alkenyl functional polyorganosiloxanes include, but are not limited to:

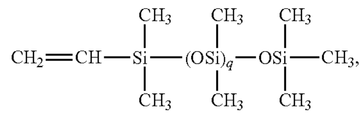

where subscript q has a value up to 1,500. Other treating agents include mono-endcapped alkoxy functional polydiorganosiloxanes, i.e., polydiorganosiloxanes having an alkoxy group at one end. Such treating agents are exemplified by the formula: $R^{25}R^{26}_{2}SiO(R^{26}_{2}SiO)_{u}Si(OR^{27})_{3}$, where subscript u has a value of 0 to 100, alternatively 1 to 50, alternatively 1 to 10, and alternatively 3 to 6. Each $R^{25}$ is independently selected from an alkyl group, such as methyl, ethyl, propyl, butyl, hexyl, and octyl; and an alkenyl group, such as vinyl, allyl, butenyl, and hexenyl. Each $R^{26}$ is independently an alkyl group such as methyl, ethyl, propyl, butyl, hexyl, and octyl. Each $R^{27}$ is independently an alkyl group such as methyl, ethyl, propyl, and butyl. Alternatively, each $R^{25}$, each $R^{26}$, and each $R^{27}$ is a methyl group. Alternatively, each $R^{25}$ is a vinyl group. Alternatively, each $R^{26}$ and each $R^{27}$ is a methyl group.

Alternative, a polyorganosiloxane capable of hydrogen bonding is useful as a treating agent. This strategy to treating surface of a filler takes advantage of multiple hydrogen bonds, either clustered or dispersed or both, as the means to tether the compatibilization moiety to the filler surface. The polyorganosiloxane capable of hydrogen bonding has an average, per molecule, of at least one silicon-bonded group capable of hydrogen bonding. The group may be selected from: an organic group having multiple hydroxyl functionalities or an organic group having at least one amino functional group. The polyorganosiloxane capable of hydrogen bonding means that hydrogen bonding is the primary mode of attachment for the polyorganosiloxane to a filler. The polyorganosiloxane may be incapable of forming covalent bonds with the filler. The polyorganosiloxane capable of hydrogen bonding may be selected from the group consisting of a saccharide-siloxane polymer, an amino-functional polyorganosiloxane, and a combination thereof. Alternatively, the polyorganosiloxane capable of hydrogen bonding may be a saccharide-siloxane polymer.

Ingredient (H) is a biocide. The amount of ingredient (H) will vary depending on factors including the type of biocide selected and the benefit desired. However, the amount of ingredient (H) may range from greater than 0% to 5% based on the weight of all ingredients in the composition. Ingredient (H) is exemplified by (h1) a fungicide, (h2) an herbicide, (h3) a pesticide, (h4) an antimicrobial agent, or a combination thereof.

Ingredient (h1) is a fungicide, for example, these include N-substituted benzimidazole carbamate, benzimidazolyl carbamate such as methyl 2-benzimidazolylcarbamate, ethyl 2-benzimidazolylcarbamate, isopropyl 2-benzimidazolylcarbamate, methyl N-{2-[1-(N,N-dimethylcarbamoyl)benzimidazolyl]}carbamate, methyl N-{2-[1-(N,N-dimethylcarbamoyl)-6-methylbenzimidazolyl]}carbamate, methyl N-{2-[1-(N,N-dimethylcarbamoyl)-5-methylbenzimidazolyl]}carbamate, methyl N-{2-[1-(N-methylcarbamoyl)benzimidazolyl]}carbamate, methyl N-{2-[1-(N-methylcarbamoyl)-6-methylbenzimidazolyl]}carbamate, methyl N-{2-[1-(N-methylcarbamoyl)-5-methylbenzimidazolyl]}carbamate, ethyl N-{2-[1-(N,N-dimethylcarbamoyl)benzimidazolyl]}carbamate, ethyl N-{2-[2-(N-methylcarbamoyl)benzimidazolyl]}carbamate, ethyl N-{2-[1-(N,N-dimethylcarbamoyl)-6-methylbenzimidazolyl]}carbamate, ethyl N-{2-[1-(N-methylcarbamoyl)-6-methylbenzimidazolyl]}carbamate, isopropyl N-{2-[1-(N,N-dimethylcarbamoyl)benzimidazolyl]}carbamate, isopropyl N-{2-[1-(N-methylcarbamoyl)benzimidazolyl]}carbamate, methyl N-{2-[1-(N-propylcarbamoyl)benzimidazolyl]}carbamate, methyl N-{2-[1-(N-butylcarbamoyl)benzimidazolyl]}carbamate, methoxyethyl N-{2-[1-(N-propylcarbamoyl)benzimidazolyl]}carbamate, methoxyethyl N-{2-[1-(N-butylcarbamoyl)benzimidazolyl]} carbamate, ethoxyethyl N-{2-[1-(N-propylcarbamoyl)benzimidazolyl]}carbamate, ethoxyethyl N-{2-[1-(N-butylcarbamoyl)benzimidazolyl]}carbamate, methyl N-{1-(N,N-dimethylcarbamoyloxy)benzimidazolyl]}carbamate, methyl N-{2-[N-methylcarbamoyloxy)benzimidazolyl]}carbamate, methyl N-{2-[1-(N-butylcarbamoyloxy)benzoimidazolyl]} carbamate, ethoxyethyl N-{2-[1-(N-propylcarbamoyl)benzimidazolyl]}carbamate, ethoxyethyl N-{2-[1-(N-butylcarbamoyloxy)benzoimidazolyl]}carbamate, methyl N-{2-[1-(N,N-dimethylcarbamoyl)-6-chlorobenzimidazolyl]} carbamate, and methyl N-{2-[1-(N,N-dimethylcarbamoyl)-6-nitrobenzimidazolyl]}carbamate; 10,10'-oxybisphenoxarsine (which has trade name Vinyzene, OBPA), di-iodomethyl-para-tolylsulfone, benzothiophene-2-cyclohexylcarboxamide-S,S-dioxide, N-(fluordichloridemethylthio)phthalimide (which has trade names Fluor-Folper, and Preventol A3); methyl-benzimideazol-2-ylcarbamate (which has trade names Carbendazim, and Preventol BCM), zinc-bis(2-pyridylthio-1-oxide) (zinc pyrithion) 2-(4-thiazolyl)-benzimidazol, N-phenyl-iodpropargylcarbamate, N-octyl-4-isothiazolin-3-on, 4,5-dichloride-2-n-octyl-4-isothiazolin-3-on, N-butyl-1,2-benzisothiazolin-3-on and/or triazolyl-compounds, such as tebuconazol in combination with zeolites containing silver.

Ingredient (h2) is an herbicide, for example, suitable herbicides include amide herbicides such as allidochlor N,N-diallyl-2-chloroacetamide; CDEA 2-chloro-N,N-diethylacetamide; etnipromid (RS)-2-[5-(2,4-dichlorophenoxy)-2-nitrophenoxy]-N-ethylpropionamide; anilide herbicides such as cisanilide cis-2,5-dimethylpyrrolidine-1-carboxanilide; flufenacet 4'-fluoro-N-isopropyl-2-[5-(trifluoromethyl)-1,3,4-thiadiazol-2-yloxy]acetanilide; naproanilide (RS)-a-2-naphthoxypropionanilide; arylalanine herbicides such as benzoylprop N-benzoyl-N-(3,4-dichlorophenyl)-DL-alanine; flamprop-M N-benzoyl-N-(3-chloro-4-fluorophenyl)-D-alanine; chloroacetanilide herbicides such as butachlor N-butoxymethyl-2-chloro-2',6'-diethylacetanilide; metazachlor 2-chloro-N-(pyrazol-1-ylmethyl)acet-2',6'-xylidide; prynachlor (RS)-2-chloro-N-(1-methylprop-2-ynyl)acetanilide; sulphonanilide herbicides such as cloransulam 3-chloro-2-(5-ethoxy-7-fluoro[1,2,4]triazolo[1,5-c]pyrimidin-2-ylsulphonamido)benzoic acid; metosulam 2',6'-dichloro-5,7-dimethoxy-3'-methyl[1,2,4]triazolo[1,5-a]pyrimidine-2-sulphonanilide; antibiotic herbicides such as bilanafos 4-[hydroxy(methyl)phosphinoyl]-L-homoalanyl-L-alanyl-L-alanine; benzoic acid herbicides such as chloramben 3-amino-2,5-dichlorobenzoic acid; 2,3,6-TBA 2,3,6-trichlorobenzoic acid; pyrimidinyloxybenzoic acid herbicides such as bispyribac 2,6-bis(4,6-dimethoxypyrimidin-2-yloxy)benzoic acid; pyrimidinylthiobenzoic acid herbicides such as pyrithiobac 2-chloro-6-(4,6-dimethoxypyrimidin-2-ylthio) benzoic acid; phthalic acid herbicides such as chlorthal tetrachloroterephthalic acid; picolinic acid herbicides such as aminopyralid 4-amino-3,6-dichloropyridine-2-carboxylic acid; quinolinecarboxylic acid herbicides such as quinclorac 3,7-dichloroquinoline-8-carboxylic acid; arsenical herbicides such as CMA calcium bis(hydrogen methylarsonate); MAMA ammonium hydrogen methylarsonate; sodium arsenite; benzoylcyclohexanedione herbicides such as mesotrione 2-(4-mesyl-2-nitrobenzoyl)cyclohexane-1,3-dione; benzofuranyl alkylsulphonate herbicides such as benfuresate 2,3-dihydro-3,3-dimethylbenzofuran-5-yl ethanesulphonate; carbamate herbicides such as carboxazole methyl 5-tert-butyl-1,2-oxazol-3-ylcarbamate; fenasulam methyl 4-[2-(4-chloro-o-tolyloxy)acetamido]phenylsulphonylcarbamate; carbanilate herbicides such as BCPC (RS)-sec-butyl 3-chlorocarbanilate; desmedipham ethyl 3-phenylcarbamoyloxyphenylcarbamate; swep methyl 3,4-dichlorocarbanilate; cyclohexene oxime herbicides such as butroxydim (RS)-(EZ)-5-(3-butyryl-2,4,6-trimethylphenyl)-2-(1-ethoxyiminopropyl)-3-hydroxycyclohex-2-en-1-one; tepraloxydim (RS)-(EZ)-2-{1-[(2E)-3-chloroallyloxyimino]propyl}-3-hydroxy-5-perhydropyran-4-ylcyclohex-2-en-1-one; cyclopropylisoxazole herbicides such as isoxachlortole 4-chloro-2-mesylphenyl 5-cyclopropyl-1,2-oxazol-4-yl ketone; dicarboximide herbicides such as flumezin 2-methyl-4-(α,α,α-trifluoro-m-tolyl)-1,2,4-oxadiazinane-3,5-dione; dinitroaniline herbicides such as ethalfluralin N-ethyl-α,α,α-trifluoro-N-(2-methylallyl)-2,6-dinitro-p-toluidine; prodiamine 5-dipropylamino-α,α,α-trifluoro-4,6-dinitro-o-toluidine; dinitrophenol herbicides such as dinoprop 4,6-dinitro-o-cymen-3-ol; etinofen α-ethoxy-4,6-dinitro-o-cresol; diphenyl ether herbicides such as ethoxyfen O-[2-chloro-5-(2-chloro-α,α,α-trifluoro-p-tolyloxy)benzoyl]-L-lactic acid; nitrophenyl ether herbicides such as aclonifen 2-chloro-6-nitro-3-phenoxyaniline; nitrofen 2,4-dichlorophenyl 4-nitrophenyl ether; dithiocarbamate herbicides such as dazomet 3,5-dimethyl-1,3,5-thiadiazinane-2-thione; halogenated aliphatic herbicides such as dalapon 2,2-dichloropropionic acid; chloroacetic acid; imidazolinone herbicides such as imazapyr (RS)-2-(4-isopropyl-4-methyl-5-oxo-2-imidazolin-2-yl) nicotinic acid; inorganic herbicides such as disodium tetraborate decahydrate; sodium azide; nitrile herbicides such as chloroxynil 3,5-dichloro-4-hydroxybenzonitrile; ioxynil 4-hydroxy-3,5-di-iodobenzonitrile; organophosphorus herbicides such as anilofos S-4-chloro-N-isopropylcarbaniloylmethyl O,O-dimethyl phosphorodithioate; glufosinate 4-[hydroxy(methyl)phosphinoyl]-DL-homoalanine; phenoxy herbicides such as clomeprop (RS)-2-(2,4-dichloro-m-tolyloxy)propionanilide; fenteracol 2-(2,4,5-trichlorophenoxy) ethanol; phenoxyacetic herbicides such as MCPA (4-chloro-2-methylphenoxy)acetic acid; phenoxybutyric herbicides such as MCPB 4-(4-chloro-o-tolyloxy)butyric acid; phenoxypropionic herbicides such as fenoprop (RS)-2-(2,4,5-trichlorophenoxy)propionic acid; aryloxyphenoxypropionic herbicides such as isoxapyrifop (RS)-2-[2-[4-(3,5-dichloro-2-pyridyloxy)phenoxy]propionyl]isoxazolidine; phenylenediamine herbicides such as dinitramine $N^1$,$N^1$-diethyl-2,6-dinitro-4-trifluoromethyl-m-phenylenediamine, pyrazolyloxyacetophenone herbicides such as pyrazoxyfen 2-[4-(2,4-dichlorobenzoyl)-1,3-dimethylpyrazol-5-yloxy] acetophenone; pyrazolylphenyl herbicides such as pyraflufen 2-chloro-5-(4-chloro-5-difluoromethoxy-1-methylpyrazol-3-yl)-4-fluorophenoxyacetic acid; pyridazine herbicides such as pyridafol 6-chloro-3-phenylpyridazin-4-ol; pyridazinone herbicides such as chloridazon 5-amino-4-chloro-2-phenylpyridazin-3(2H)-one; oxapyrazon 5-bromo-1,6-dihydro-6-oxo-1-phenylpyridazin-4-yloxamic acid; pyridine herbicides such as fluroxypyr 4-amino-3,5-dichloro-6-fluoro-2-pyridyloxyacetic acid; thiazopyr methyl 2-difluoromethyl-5-(4,5-dihydro-1,3-thiazol-2-yl)-4-isobutyl-6-trifluoromethylnicotinate; pyrimidinediamine herbicides such as iprymidam 6-chloro-$N^4$-isopropylpyrimidine-2,4-diamine; quaternary ammonium herbicides such as diethamquat 1,1'-bis(diethylcarbamoylmethyl)-4,4'-bipyridinium; paraquat 1,1'-dimethyl-4,4'-bipyridinium; thiocarbamate herbicides such as cycloate S-ethyl cyclohexyl(ethyl)thiocarbamate; tiocarbazil S-benzyl di-sec-butylthiocarbamate; thiocarbonate herbicides such as EXD O,O-diethyl dithiobis (thioformate); thiourea herbicides such as methiuron 1,1-dimethyl-3-m-tolyl-2-thiourea; triazine herbicides such as triaziflam (RS)—N-[2-(3,5-dimethylphenoxy)-1-methylethyl]-6-(1-fluoro-1-methylethyl)-1,3,5-triazine-2,4-diamine; chlorotriazine herbicides such as cyprazine 6-chloro-$N^2$-cyclopropyl-$N^4$-isopropyl-1,3,5-triazine-2,4-diamine; propazine 6-chloro-$N^2$,$N^4$-di-isopropyl-1,3,5-triazine-2,4-diamine; methoxytriazine herbicides such as prometon $N^2$,$N^4$-di-isopropyl-6-methoxy-1,3,5-triazine-2,4-diamine; methylthiotriazine herbicides such as cyanatryn 2-(4-ethylamino-6-methylthio-1,3,5-triazin-2-ylamino)-2-methylpropionitrile; triazinone herbicides such as hexazinone 3-cyclohexyl-6-dimethylamino-1-methyl-1,3,5-triazine-2,4(1H, 3H)-dione; triazole herbicides such as epronaz N-ethyl-N- propyl-3-propylsulphonyl-1H-1,2,4-triazole-1-carboxamide; triazolone herbicides such as carfentrazone (RS)-2-chloro-3-{2-chloro-5-[4-(difluoromethyl)-4,5-dihydro-3-methyl-5-oxo-1H-1,2,4-triazol-1-yl]-4-fluorophenyl}propionic acid; triazolopyrimidine herbicides such as florasulam 2',6',8-trifluoro-5-methoxy[1,2,4]triazolo[1,5-c]pyrimidine-2-sulphonanilide; uracil herbicides such as flupropacil isopropyl 2-chloro-5-(1,2,3,6-tetrahydro-3-methyl-2,6-dioxo-4-trifluoromethylpyrimidin-1-yl)benzoate; urea herbicides such as cycluron 3-cyclo-octyl-1,1-dimethylurea; monisouron 1-(5-tert-butyl-1,2-oxazol-3-yl)-3-methylurea; phenylurea herbicides such as chloroxuron 3-[4-(4-chlorophenoxy)phenyl]-1,1-dimethylurea; siduron 1-(2-methylcyclohexyl)-3-phenylurea; pyrimidinylsulphonylurea herbicides such as flazasulphuron 1-(4,6-dimethoxypyrimidin-2-yl)-3-(3-trifluoromethyl-2-pyridylsulphonyl)urea; pyrazosulphuron 5-[(4,6-dimethoxypyrimidin-2-ylcarbamoyl)sulphamoyl]-1-methylpyrazole-4-carboxylic acid; triazinylsulphonylurea herbicides such as thifensulphuron 3-(4-methoxy-6-methyl-1,3,5-triazin-2-ylcarbamoylsulphamoyl)thiophene-2-carboxylic acid; thiadiazolylurea herbicides such as tebuthiuron 1-(5-tert-butyl-1,3,4-thiadiazol-2-yl)-1,3-dimethylurea; and/or unclassified herbicides such as chlorfenac (2,3,6-trichlorophenyl)acetic acid; methazole 2-(3,4-dichlorophenyl)-4-methyl-1,2,4-oxadiazolidine-3,5-dione; tritac (RS)-1-(2,3,6-trichlorobenzyloxy)propan-2-ol; 2,4-D, chlorimuron, and fenoxaprop; and combinations thereof.

Ingredient (h3) is a pesticide. Suitable pesticides are exemplified by atrazine, diazinon, and chlorpyrifos. For purposes of this application, pesticide includes insect repellents such as N,N-diethyl-meta-toluamide and pyrethroids such as pyrethrin.

Ingredient (h4) is an antimicrobial agent. Suitable antimicrobials are commercially available, such as DOW CORNING® 5700 and DOW CORNING® 5772, which are from Dow Corning Corporation of Midland, Mich., U.S.A.

Alternatively, ingredient (H) may comprise a boron containing material, e.g., boric anhydride, borax, or disodium octaborate tetrahydrate; which may function as a pesticide, fungicide, and/or flame retardant.

Ingredient (I) is a stabilizer that may be used for slowing the reaction rate of the composition, as compared to a composition containing the same ingredients but with the stabilizer omitted. Stabilizers for hydrosilylation curable compositions are exemplified by acetylenic alcohols such as methyl butynol, ethynyl cyclohexanol, dimethyl hexynol, and 3,5-dimethyl-1-hexyn-3-ol, 1-butyn-3-ol, 1-propyn-3-ol, 2-methyl-3-butyn-2-ol, 3-methyl-1-butyn-3-ol, 3-methyl-1-pentyn-3-ol, 3-phenyl-1-butyn-3-ol, 4-ethyl-1-octyn-3-ol, 3,5-dimethyl-1-hexyn-3-ol, and 1-ethynyl-1-cyclohexanol, and a combination thereof; cycloalkenylsiloxanes such as methylvinylcyclosiloxanes exemplified by 1,3,5,7-tetramethyl-1,3,5,7-tetravinylcyclotetrasiloxane, 1,3,5,7-tetramethyl-1,3,5,7-tetrahexenylcyclotetrasiloxane, and a combination thereof; ene-yne compounds such as 3-methyl-3-penten-1-yne, 3,5-dimethyl-3-hexen-1-yne; triazoles such as benzotriazole; phosphines; mercaptans; hydrazines; amines such as tetramethyl ethylenediamine, dialkyl fumarates, dialkenyl fumarates, dialkoxyalkyl fumarates, maleates such as diallyl maleate; nitriles; ethers; carbon monoxide; alkenes such as cyclo-octadiene; divinyltetramethyldisiloxane; alcohols such as benzyl alcohol; and a combination thereof.

Alternatively, ingredient (I) in the composition may be a silylated acetylenic compound. Without wishing to be bound by theory, it is thought that adding a silylated acetylenic compound reduces yellowing of the reaction product prepared from hydrosilylation reaction of the composition as compared to a reaction product from hydrosilylation of a composition that does not contain a silylated acetylenic compound or that contains an organic acetylenic alcohol stabilizer, such as those described above.

The silylated acetylenic compound is exemplified by (3-methyl-1-butyn-3-oxy)trimethylsilane, ((1,1-dimethyl-2-propynyl)oxy)trimethylsilane, bis(3-methyl-1-butyn-3-oxy)dimethylsilane, bis(3-methyl-1-butyn-3-oxy)silanemethylvinylsilane, bis((1,1-dimethyl-2-propynyl)oxy)dimethylsilane, methyl(tris(1,1-dimethyl-2-propynyloxy))silane, methyl(tris(3-methyl-1-butyn-3-oxy))silane, (3-methyl-1-butyn-3-oxy)dimethylphenylsilane, (3-methyl-1-butyn-3-oxy)dimethylhexenylsilane, (3-methyl-1-butyn-3-oxy)triethylsilane, bis(3-methyl-1-butyn-3-oxy)methyltrifluoropropylsilane, (3,5-dim ethyl-1-hexyn-3-oxy)trimethylsilane, (3-phenyl-1-butyn-3-oxy)diphenylmethylsilane, (3-phenyl-1-butyn-3-oxy)dimethylphenylsilane, (3-phenyl-1-butyn-3-oxy)dimethylvinylsilane, (3-phenyl-1-butyn-3-oxy)dimethylhexenylsilane, (cyclohexyl-1-ethyn-1-oxy)dimethylhexenylsilane, (cyclohexyl-1-ethyn-1-oxy)dimethylvinylsilane, (cyclohexyl-1-ethyn-1-oxy)diphenylmethylsilane, (cyclohexyl-1-ethyn-1-oxy)trimethylsilane, and combinations thereof. Alternatively, ingredient (I) is exemplified by methyl(tris(1,1-dimethyl-2-propynyloxy))silane, ((1,1-dimethyl-2-propynyl)oxy)trimethylsilane, or a combination thereof. The silylated acetylenic compound useful as ingredient (I) may be prepared by methods known in the art, such as silylating an acetylenic alcohol described above by reacting it with a chlorosilane in the presence of an acid receptor.

The amount of stabilizer added to the composition will depend on various factors including the desired pot life of the composition, whether the composition will be a one part composition or a multiple part composition, the particular stabilizer used, and the selection and amount of ingredient (C), if present. However, when present, the amount of stabilizer may range from 0% to 5%, alternatively 0% to 1%, alternatively 0.001% to 1%, alternatively 0.01% to 0.5%, and alternatively 0.0025% to 0.025%, based on the weight of all ingredients in the composition.

Ingredient (J) is a flame retardant. Suitable flame retardants may include, for example, carbon black, hydrated aluminum hydroxide, and silicates such as wollastonite, platinum and platinum compounds. Alternatively, the flame retardant may be selected from halogen based flame-retardants such as decabromodiphenyloxide, octabromodiphenyl oxide, hexabromocyclododecane, decabromobiphenyl oxide, diphenyoxybenzene, ethylene bis-tetrabromophthalmide, pentabromoethyl benzene, pentabromobenzyl acrylate, tribromophenyl maleic imide, tetrabromobisphenyl A, bis-(tribromophenoxy) ethane, bis-(pentabromophenoxy) ethane, polydibomophenylene oxide, tribromophenylallyl ether, bis-dibromopropyl ether, tetrabromophthalic anhydride, dibromoneopentyl gycol, dibromoethyl dibromocyclohexane, pentabromodiphenyl oxide, tribromostyrene, pentabromochlorocyclohexane, tetrabromoxylene, hexabromocyclododecane, brominated polystyrene, tetradecabromodiphenoxybenzene, trifluoropropene and PVC. Alternatively, the flame retardant may be selected from phosphorus based flame-retardants such as (2,3-dibromopropyl)-phosphate, phosphorus, cyclic phosphates, triaryl phosphate, bis-melaminium pentate, pentaerythritol bicyclic phosphate, dimethyl methyl phosphate, phosphine oxide diol, triphenyl phosphate, tris-(2-chloroethyl) phosphate, phosphate esters such as tricreyl, trixylenyl, isodecyl diphenyl, ethylhexyl diphenyl, phosphate salts of various amines such as ammonium phosphate, trioctyl, tributyl or tris-butoxyethyl phosphate ester. Other flame retardants may include tetraalkyl lead compounds such as tetraethyl lead, iron pentacarbonyl, manganese methyl cyclopentadienyl tricarbonyl, melamine and derivatives such as melamine salts, guanidine, dicyandiamide, ammonium sulphamate, alumina trihydrate, and magnesium hydroxide alumina trihydrate.

The amount of flame retardant will vary depending on factors such as the flame retardant selected and whether solvent is present. However, the amount of flame retardant in the composition may range from greater than 0% to 10% based on the weight of all ingredients in the composition.

Ingredient (K) is a surface modifier. Suitable surface modifiers are exemplified by (k1) an adhesion promoter and (k2) a release agent. Suitable adhesion promoters for ingredient (k1) may comprise a transition metal chelate, a hydrocarbonoxysilane such as an alkoxysilane, a combination of an alkoxysilane and a hydroxy-functional polyorganosiloxane, an aminofunctional silane, or a combination thereof. Adhesion promoters are known in the art and may comprise silanes having the formula $R^{19}{}_{r}R^{20}{}_{s}Si(OR^{21})_{4-(r+s)}$ where each $R^{19}$ is independently a monovalent organic group having at least 3 carbon atoms; $R^{20}$ contains at least one SiC bonded substituent having an adhesion-promoting group, such as amino, epoxy, mercapto or acrylate groups; subscript r has a value ranging from 0 to 2; subscript s is either 1 or 2; and the sum of (r+s) is not greater than 3. Each $R^{21}$ is independently a saturated hydrocarbon group. Saturated hydrocarbon groups for $R^{21}$ may be, for example, an alkyl group of 1 to 4 carbon atoms, alternatively 1 to 2 carbon atoms. $R^{21}$ is exemplified by methyl, ethyl, propyl, and butyl. Alternatively, the adhesion promoter may comprise a partial condensate of the above silane. Alternatively, the adhesion promoter may comprise a combination of an alkoxysilane and a hydroxy-functional polyorganosiloxane.

Alternatively, the adhesion promoter may comprise an unsaturated or epoxy-functional compound. The adhesion promoter may comprise an unsaturated or epoxy-functional alkoxysilane. For example, the functional alkoxysilane can have the formula $R^{22}{}_{t}Si(OR^{23})_{(4-t)}$, where subscript t is 1, 2, or 3, alternatively subscript t is 1. Each $R^{22}$ is independently a monovalent organic group with the proviso that at least one $R^{22}$ is an unsaturated organic group or an epoxy-functional organic group. Epoxy-functional organic groups for $R^{22}$ are exemplified by 3-glycidoxypropyl and (epoxycyclohexyl) ethyl. Unsaturated organic groups for $R^{22}$ are exemplified by 3-methacryloyloxypropyl, 3-acryloyloxypropyl, and unsaturated monovalent hydrocarbon groups such as vinyl, allyl, hexenyl, undecylenyl. Each $R^{23}$ is independently a saturated hydrocarbon group of 1 to 4 carbon atoms, alternatively 1 to 2 carbon atoms. $R^{23}$ is exemplified by methyl, ethyl, propyl, and butyl.

Examples of suitable epoxy-functional alkoxysilanes include 3-glycidoxypropyltrimethoxysilane, 3-glycidoxypropyltriethoxysilane, (epoxycyclohexyl)ethyldimethoxysilane, (epoxycyclohexyl)ethyldiethoxysilane and combinations thereof. Examples of suitable unsaturated alkoxysilanes include vinyltrimethoxysilane, allyltrimethoxysilane, allyltriethoxysilane, hexenyltrimethoxysilane, undecylenyltrimethoxysilane, 3-methacryloyloxypropyl trimethoxysilane, 3-methacryloyloxypropyl triethoxysilane, 3-acryloyloxypropyl trimethoxysilane, 3-acryloyloxypropyl triethoxysilane, and combinations thereof.

Alternatively, the adhesion promoter may comprise an epoxy-functional siloxane such as a reaction product of a hydroxy-terminated polyorganosiloxane with an epoxy-functional alkoxysilane, as described above, or a physical blend of the hydroxy-terminated polyorganosiloxane with the epoxy-functional alkoxysilane. The adhesion promoter may comprise a combination of an epoxy-functional alkoxysilane and an epoxy-functional siloxane. For example, the adhesion promoter is exemplified by a mixture of 3-glycidoxypropyltrimethoxysilane and a reaction product of hydroxy-terminated methylvinylsiloxane with 3-glycidoxypropyltrimethoxysilane, or a mixture of 3-glycidoxypropyltrimethoxysilane and a hydroxy-terminated methylvinylsiloxane, or a mixture of 3-glycidoxypropyltrimethoxysilane and a hydroxy-terminated methylvinyl/dimethylsiloxane copolymer.

Alternatively, the adhesion promoter may comprise an aminofunctional silane, such as an aminofunctional alkoxysilane exemplified by $H_2N(CH_2)_2Si(OCH_3)_3$, $H_2N(CH_2)_2Si(OCH_2CH_3)_3$, $H_2N(CH_2)_3Si(OCH_3)_3$, $H_2N(CH_2)_3Si(OCH_2CH_3)_3$, $CH_3NH(CH_2)_3Si(OCH_3)_3$, $CH_3NH(CH_2)_3Si(OCH_2CH_3)_3$, $CH_3NH(CH_2)_5Si(OCH_3)_3$, $CH_3NH(CH_2)_5Si(OCH_2CH_3)_3$, $H_2N(CH_2)_2NH(CH_2)_3Si(OCH_3)_3$, $H_2N(CH_2)_2NH(CH_2)_3Si(OCH_2CH_3)_3$, $CH_3NH(CH_2)_2NH(CH_2)_3Si(OCH_3)_3$, $CH_3NH(CH_2)_2NH(CH_2)_3Si(OCH_2CH_3)_3$, $C_4H_9NH(CH_2)_2NH(CH_2)_3Si(OCH_3)_3$, $C_4H_9NH(CH_2)_2NH(CH_2)_3Si(OCH_2CH_3)_3$, $H_2N(CH_2)_2SiCH_3(OCH_3)_2$, $H_2N(CH_2)_2SiCH_3(OCH_2CH_3)_2$, $H_2N(CH_2)_3SiCH_3(OCH_3)_2$, $H_2N(CH_2)_3SiCH_3(OCH_2CH_3)_2$, $CH_3NH(CH_2)_3SiCH_3(OCH_3)_2$, $CH_3NH(CH_2)_3SiCH_3(OCH_2CH_3)_2$, $CH_3NH(CH_2)_5SiCH_3(OCH_3)_2$, $CH_3NH(CH_2)_5SiCH_3(OCH_2CH_3)_2$, $H_2N(CH_2)_2NH(CH_2)_3SiCH_3(OCH_3)_2$, $H_2N(CH_2)_2NH(CH_2)_3SiCH_3(OCH_2CH_3)_2$, $CH_3NH(CH_2)_2NH(CH_2)_3SiCH_3(OCH_3)_2$, $CH_3NH(CH_2)_2NH(CH_2)_3SiCH_3(OCH_2CH_3)_2$, $C_4H_9NH(CH_2)_2NH(CH_2)_3SiCH_3(OCH_3)_2$, $C_4H_9NH(CH_2)_2NH(CH_2)_3SiCH_3(OCH_2CH_3)_2$, and a combination thereof.

Alternatively, the adhesion promoter may comprise a transition metal chelate. Suitable transition metal chelates include titanates, zirconates such as zirconium acetylacetonate, aluminum chelates such as aluminum acetylacetonate, and combinations thereof. Alternatively, the adhesion promoter may comprise a combination of a transition metal chelate with an alkoxysilane, such as a combination of glycidoxypropyltrimethoxysilane with an aluminum chelate or a zirconium chelate.

Ingredient (k2) is a release agent. Suitable release agents are exemplified by fluorinated compounds, such as fluoro-functional silicones, or fluoro-functional organic compounds.

Alternatively, the surface modifier for ingredient (K) may be used to change the appearance of the surface of a reaction product of the composition. For example, surface modifier may be used to increase gloss of the surface of a reaction product of the composition. Such a surface modifier may comprise a polydiorganosiloxane with alkyl and aryl groups. For example, DOW CORNING@ 550 Fluid is a trimethylsiloxy-terminated poly(dimethyl/methylphenyl)siloxane with a viscosity of 125 cSt that is commercially available from Dow Corning Corporation of Midland, Mich., U.S.A.

Alternatively, ingredient (K) may be a natural oil obtained from a plant or animal source, such as linseed oil, tung oil, soybean oil, castor oil, fish oil, hempseed oil, cottonseed oil, oiticica oil, or rapeseed oil.

The exact amount of ingredient (K) depends on various factors including the type of surface modifier selected as ingredient (K) and the end use of the composition and its reaction product. However, ingredient (K), when present, may be added to the composition in an amount ranging from 0.01 to 50 weight parts based on the weight of the composition, alternatively 0.01 to 10 weight parts, and alternatively 0.01 to 5 weight parts. Ingredient (K) may be one adhesion promoter. Alternatively, ingredient (K) may comprise two or more different surface modifiers that differ in at least one of the following properties: structure, viscosity, average molecular weight, polymer units, and sequence.

Chain lengtheners may include difunctional silanes and difunctional siloxanes, which extend the length of polyorganosiloxane chains before crosslinking occurs. Chain lengtheners may be used to reduce the modulus of elongation of the cured product. Chain lengtheners compete in their reactions with aliphatically unsaturated groups and/or silicon bonded hydrogen atoms in other ingredients of the composition, e.g., ingredients (B) and/or ingredient (C), when present. Dimethylhydrogensiloxy-terminated polydimethylsiloxanes having relatively low degrees of polymerization (e.g., DP ranging from 3 to 50) may be used as ingredient (L). Ingredient (L) may be one chain lengthener Alternatively, ingredient (L) may comprise two or more different chain lengtheners that differ in at least one of the following properties: structure, viscosity, average molecular weight, polymer units, and sequence Ingredient (M) is and endblocker comprising an M-unit, i.e., a siloxane unit of formula $R^{24}{}_3SiO_{1/2}$, where each $R^{24}$ independently represents a monovalent, non-functional, organic group, such as a monovalent hydrocarbon group free of aliphatic unsaturation. Ingredient (M) may comprise polyorganosiloxanes endblocked on one terminal end by a triorganosilyl group, e.g., $(CH_3)_3SiO$—, and on the other end by a silicon bonded hydrogen atom and/or an aliphatically unsaturated organic group. Ingredient (M) may be a polydiorganosiloxane such as a polydimethylsiloxane. The polydiorganosiloxanes having both silicon bonded hydrogen terminals and triorganosilyl end groups, may have more than 50%, alternatively more than 75%, of the total end groups as silicon bonded hydrogen atoms. The amount of triorganosilyl group in the polydimethylsiloxane may be used to regulate the modulus of a cured product prepared by curing the composition. Without wishing to be bound by theory, it is thought that higher concentrations of triorganosilyl end groups may provide a lower modulus in cured products. Ingredient (M) may be one endblocker. Alternatively, ingredient (M) may comprise two or more different endblockers that differ in at least one of the following properties: structure, viscosity, average molecular weight, polymer units, and sequence.

Ingredient (N) is a flux agent. The composition may comprise 0% to 2% of the flux agent based on the weight of all ingredients in the composition. Molecules containing chemically active functional groups such as carboxylic acid and amines can be used as flux agents. Such flux agents can include aliphatic acids such as succinic acid, abietic acid, oleic acid, and adipic acid; aromatic acids such as benzoic acids; aliphatic amines and their derivatives, such as triethanolamine, hydrochloride salts of amines, and hydrobromide salts of amines. Flux agents are known in the art and are commercially available.

Ingredient (O) is an anti-aging additive. The anti-aging additive may comprise an antioxidant, a UV absorber, a UV stabilizer, a heat stabilizer, or a combination thereof. Suitable antioxidants are known in the art and are commercially available. Suitable antioxidants include phenolic antioxidants and combinations of phenolic antioxidants with stabilizers. Phenolic antioxidants include fully sterically hindered phenols and partially hindered phenols; and sterically hindered amines such as tetramethyl-piperidine derivatives. Suitable phenolic antioxidants include vitamin E and IRGANOX® 1010 from Ciba Specialty Chemicals, U.S.A. IRGANOX® 1010 comprises pentaerythritol tetrakis(3-(3,5-di-t-butyl-4-hydroxyphenyl)propionate). Examples of UV absorbers include phenol, 2-(2H-benzotriazol-2-yl)-6-dodecyl-4-methyl-, branched and linear (TINUVIN® 571). Examples of UV stabilizers include bis(1,2,2,6,6-pentamethyl-4-piperidyl) sebacate; methyl 1,2,2,6,6-pentamethyl-4-piperidyl/sebacate; and a combination thereof (TINUVIN® 272). These and other TINUVIN® additives, such as TINUVIN® 765 are commercially available from Ciba Specialty Chemicals of Tarrytown, N.Y., U.S.A. Other UV and light stabilizers are commercially available, and are exemplified by LowLite from Chemtura, OnCap from PolyOne, and Light Stabilizer 210 from E. I. du Pont de Nemours and Company of Delaware, U.S.A. Oligomeric (higher molecular weight) stabilizers may alternatively be used, for example, to minimize potential for migration of the stabilizer out of the composition or the cured product thereof. An example of an oligomeric antioxidant stabilizer (specifically, hindered amine light stabilizer (HALS)) is Ciba TINUVIN® 622, which is a dimethylester of butanedioic acid copolymerized with 4-hydroxy-2,2,6,6-tetramethyl-1-piperidine ethanol. Heat stabilizers may include iron oxides and carbon blacks, iron carboxylate salts, cerium hydrate, barium zirconate, cerium and zirconium octoates, and porphyrins.

The amount of ingredient (O) depends on various factors including the specific anti-aging additive selected and the anti-aging benefit desired. However, the amount of ingredient (O) may range from 0 to 5 weight %, alternatively 0.1% to 4%, and alternatively 0.5 to 3 weight %, based on the weight of all ingredients in the composition. Ingredient (O) may be one anti-aging additive. Alternatively, ingredient (0) may comprise two or more different anti-aging additives.

Ingredient (P) is a pigment. For purposes of this application, the term 'pigment' includes any ingredient used to impart color to a reaction product of a composition described herein. The amount of pigment depends on various factors including the type of pigment selected and the desired degree of coloration of the product. For example, the composition may comprise 0 to 20%, alternatively 0.001% to 5%, of a pigment based on the weight of all ingredients in the composition.

Examples of suitable pigments include indigo, titanium dioxide Stan-Tone 50SP01 Green (which is commercially available from PolyOne) and carbon black. Representative, non-limiting examples of carbon black include Shawinigan Acetylene black, which is commercially available from Chevron Phillips Chemical Company LP; SUPERJET® Carbon Black (LB-1011) supplied by Elementis Pigments Inc., of Fairview Heights, Ill. U.S.A.; SR 511 supplied by Sid Richardson Carbon Co, of Akron, Ohio U.S.A.; and N330, N550, N762, N990 (from Degussa Engineered Carbons of Parsippany, N.J., U.S.A.).

Ingredient (Q) is an acid acceptor. Suitable acid acceptors include magnesium oxide, calcium oxide, and combinations thereof. The composition may comprise 0% to 2 of ingredient (Q) based on the weight of the composition.

The composition may optionally further comprise up to 5%, alternatively 1% to 2 based on the weight of the composition of ingredient (R) a rheological additive for modifying rheology of the composition. Rheological additives are known in the art and are commercially available. Examples include polyamides, Polyvest, which is commercially available from Evonk, Disparlon from King Industries, Kevlar Fibre Pulp from Du Pont, Rheospan from Nanocor, and Ircogel from Lubrizol. Other suitable rheological additives include polyamide waxes; hydrogenated castor oil derivatives; and metal soaps such as calcium stearate, aluminum stearate and barium stearate, and combinations thereof.

Alternatively, ingredient (R) may comprise a microcrystalline wax that is a solid at 25° C. (wax). The melting point may be selected such that the wax has a melting point at the low end of the desired application temperature range. Without wishing to be bound by theory, it is thought that ingredient (R) acts as a process aid that improves flow properties of the composition. Without wishing to be bound by theory, it is thought that incorporation of wax may also facilitate incorporation of fillers, compounding and de-airing (during production of the composition), and mixing (static or dynamic mixing during application of parts of a multiple part composition). It is thought that the wax, when molten, serves as a process aid, substantially easing the incorporation of filler in the composition during compounding, the compounding process itself, as well as in during a de-airing step, if used. The wax, with a melt temperature below 100° C., may facilitate mixing of the parts of a multiple part composition before application, even in a simple static mixer.

Waxes suitable for use as ingredient (R) may be non-polar hydrocarbons. The waxes may have branched structures, cyclic structures, or combinations thereof. For example, petroleum microcrystalline waxes are available from Strahl & Pitsch, Inc., of West Babylon, N.Y., U.S.A. and include SP 96 (melting point ranging from 62° C. to 69° C.), SP 18 (melting point ranging from 73° C. to 80° C.), SP 19 (melting point ranging from 76° C. to 83° C.), SP 26 (melting point ranging from 76° C. to 83° C.), SP 60 (melting point ranging from 79° C. to 85° C.), SP 617 (melting point ranging from 88° C. to 93° C.), SP 89 (melting point ranging from 90° C. to 95° C.), and SP 624 (melting point ranging from 90° C. to 95° C.). Other petroleum microcrystalline waxes include waxes marketed under the trademark Multiwax® by Crompton Corporation of Petrolia, Pa., U.S.A. These waxes include 180-W, which comprises saturated branched and cyclic non-polar hydrocarbons and has melting point ranging from 79° C. to 87° C.; Multiwax® W-445, which comprises saturated branched and cyclic non-polar hydrocarbons, and has melting point ranging from 76° C. to 83° C.; and Multiwax® W-835, which comprises saturated branched and cyclic non-polar hydrocarbons, and has melting point ranging from 73° C. to 80° C.

The amount of ingredient (R) depends on various factors including the specific rheological additive selected and the selections of the other ingredients of the composition. However, the amount of ingredient (R) may range from 0 parts to 20 parts, alternatively 1 parts to 15 parts, and alternatively 1 part to 5 parts based on the weight of all ingredients in the composition. Ingredient (R) may be one rheological additive. Alternatively, ingredient (R) may comprise two or more different rheological additives.

A vehicle may be used in the composition. The vehicle may facilitate flow of the composition and introduction of certain ingredients, such as silicone resin. Vehicles used herein are those that help fluidize the ingredients of the composition but essentially do not react with the ingredients. The vehicle may be selected based on solubility the ingredients in the composition and volatility. The solubility refers to the vehicle being sufficient to dissolve and/or disperse ingredients of the composition. Volatility refers to vapor pressure of the vehicle. If the vehicle is too volatile (having too high vapor pressure) bubbles may form in the composition during hydrosilylation reaction, and the bubbles may cause cracks or otherwise weaken or detrimentally affect properties of the reaction product. However, if the vehicle is not volatile enough (too low vapor pressure) the vehicle may remain as a plasticizer in the reaction product of the composition.

Suitable vehicles include non-functional polyorganosiloxanes with suitable vapor pressures, such as hexamethyldisiloxane, octamethyltrisiloxane, hexamethylcyclotrisiloxane and other low molecular weight polyorganosiloxanes, such as 0.5 to 1.5 cSt Dow Corning® 200 Fluids and Dow Corning® OS FLUIDS, which are commercially available from Dow Corning Corporation of Midland, Mich., U.S.A.

Alternatively, the vehicle may comprise an organic solvent. The organic solvent can be an alcohol such as methanol, ethanol, isopropanol, butanol, or n-propanol; a ketone such as acetone, methylethyl ketone, or methyl isobutyl ketone; an aromatic hydrocarbon such as benzene, toluene, or xylene; an aliphatic hydrocarbon such as heptane, hexane, or octane; a glycol ether such as propylene glycol methyl ether, dipropylene glycol methyl ether, propylene glycol n-butyl ether, propylene glycol n-propyl ether, or ethylene glycol n-butyl ether, a halogenated hydrocarbon such as dichloromethane, 1,1,1-trichloroethane or methylene chloride; chloroform; dimethyl sulfoxide; dimethyl formamide, acetonitrile; tetrahydrofuran; white spirits; mineral spirits; naphtha; n-methyl pyrrolidone; or a combination thereof.

The amount of vehicle will depend on various factors including the type of vehicle selected and the amount and type of other ingredients selected for the composition. However, the amount of vehicle may range from 1% to 99%, alternatively 2% to 50%, based on the weight of all ingredients in the composition. Ingredient (S) can be added during preparation of the composition, for example, to aid mixing and delivery. All or a portion of ingredient (S) may optionally be removed after the composition is prepared.

Ingredient (T) is a surfactant. Suitable surfactants include silicone polyethers, ethylene oxide polymers, propylene oxide polymers, copolymers of ethylene oxide and propylene oxide, other non-ionic surfactants, and combinations thereof. The composition may comprise 0% to 0.05% of the surfactant based on the weight of all ingredients in the composition.

Ingredient (U) is a corrosion inhibitor. Examples of suitable corrosion inhibitors include benzotriazole, mercaptabenzotriazole and commercially available corrosion inhibitors such as 2,5-dimercapto-1,3,4-thiadiazole derivative (CUVAN® 826) and alkylthiadiazole (CUVAN® 484) from R. T. Vanderbilt of Norwalk, Conn., U.S.A. When present, the amount of ingredient (U) may range from 0.05% to 0.5% based on the weight of the composition.

When selecting ingredients for the composition described above, there may be overlap between types of ingredients because certain ingredients described herein may have more than one function. For example, certain alkoxysilanes may be useful as filler treating agents and as adhesion promoters, and certain plasticizers such as fatty acid esters may also be useful as filler treating agents. Certain particulates may be useful as fillers and as pigments, and even as flame retardants, e.g., carbon black. When adding additional ingredients to the composition, the additional ingredients are distinct from one another.

The composition can be prepared by a method comprising combining all ingredients by any convenient means such as mixing at ambient or elevated temperature. Ingredient (I), when present, may be added before ingredient (A), for example, when the composition will be prepared at elevated temperature and/or the composition will be prepared as a one part composition.

When ingredient (G) is present, the composition may optionally be prepared by surface treating a particulate ingredient (e.g., filler and/or spacer, if present) with ingredient (G), and thereafter mixing the product thereof with the other ingredients of the composition.

Alternatively, the composition may be prepared as a multiple part composition, for example, when ingredient (I) is absent, or when the composition will be stored for a long period of time before use. In the multiple part composition, ingredient (A) is stored in a separate part from any ingredient having a silicon bonded hydrogen atom, for example ingredient (C), and the parts are combined shortly before use of the composition. For example, a two part composition may be prepared by combining ingredients comprising (B), (A), (F), and optionally one or more other additional ingredients described above to form a base by any convenient means such as mixing. A curing agent may be prepared by combining ingredients comprising (B), (C), and optionally one or more other additional ingredients described above by any convenient means such as mixing. The ingredients may be combined at ambient or elevated temperature. When a two part composition is used, the weight ratio of amounts of base to curing agent may range from 1:1 to 10:1. The composition will react via hydrosilylation reaction to form a reaction product. The reaction product may have various forms, such as a silane, a gum, a gel, a rubber, or a resin.

EXAMPLES

These examples are intended to illustrate some embodiments of the invention and should not be interpreted as limiting the scope of the invention set forth in the claims. Reference examples should not be deemed to be prior art unless so indicated. All syntheses and manipulations were carried out under argon using standard Schlenk and vacuum techniques. $^{1}H$, $^{13}C$, and $^{29}Si$ NMR spectra were recorded on a Varian Gemini 300 VT and Varian Mercury 300 VT spectrometers in $C_6D_6$. The mass spectra of the products were determined by GC-MS (Varian Saturn 2100T equipped with a DB-1, 30 m capillary column). GC analyses were carried out on a Varian 3400 CX series gas chromatograph with a capillary column DB-1, 30 m and TC detector. All solvents and liquid reagents were dried and distilled under argon prior to use. The following ingredients are used in the examples below.

Synthesis of Iron(0) Complexes with Silicon Dienes

Example 1

Synthesis of complex C1 ([$Fe(CO)_3${$(H_2C{=}CHSiMe_2)_2O$}])

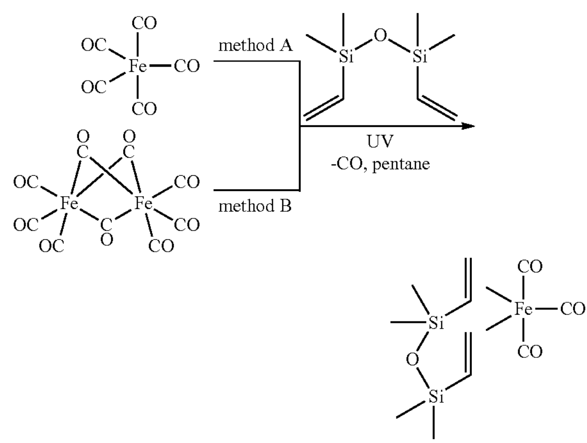

Method A

In the Schlenck's tube (Pyrex glass) equipped with magnetic stirrer condenser with oil valve 13.79 g (74 mmol) of 1,3-divinyltetramethyldisiloxane, 1.45 g (7.4 mmol) $Fe(CO)_5$ and 50 mL of pentane were placed. The mixture was irradiated with UV light for 2 hours under flow of argon. After filtration by a cannula system the solvent was evaporated form a yellow solution and yellow crystals were dried under vacuum.

$^{1}H$ NMR (300 MHz, $C_6D_6$, 300 K) δ(ppm)=3.06 (m); 2.65 (m); 2.40 (m); 1.87 (m) ($H_2C{=}CH$— coordinated); 0.178 (s, Me-)

$^{13}C$ NMR (75.42 MHz, $C_6D_6$, 300 K) δ(ppm)=211.86 (CO); 46.47; 44.11, 40.83 ($H_2C{=}CH$— coordinated); 2.45 (Me-)

Method B

In the Schlenck's tube (Pyrex glass) equipped with magnetic stirrer condenser with oil valve 2.56 g (13.74 mmol) of 1,3-divinyltetramethyldisiloxane, 0.5 g (1.37 mmol) $Fe_2(CO)_9$ and 20 mL of pentane were placed. The mixture obtained was mixed overnight and then irradiated with UV light for 2 hours under flow of argon. After filtration by a cannula system the solvent was evaporated form the yellow solution and yellow crystals were dried under vacuum.

$^{1}H$ NMR (300 MHz, $C_6D_6$, 300 K) δ(ppm)=3.07 (d); 2.60 (m); 2.38 (m) 1.85 (m) (H2C═CH-coordinated); 0.29 (s); 0.22 (s); 0.20 (s), 0.18 (s), 0.15 (s) (-Me)

$^{13}C$ NMR (75.42 MHz, $C_6D_6$, 300 K) δ(ppm)=211.90 (CO); 46.51; 44.46; 44.13; 43.97; 40.85 (H2C═CH— coordinated); 2.59; 2.52; 2.47; 2.34; 1.88, 1.40; 0.57; 0.25 (-Me)

Example 2

Synthesis of Complex C2

In the Schlenck's tube (Pyrex glass) equipped with magnetic stirrer condenser with oil valve 2.55 g (13.74 mmol) of 1,3-divinyltetramethyldisilazane, 0.5 g (1.37 mmol) $Fe_2(CO)_9$ and 20 mL of pentane were placed. The mixture obtained was mixed over-night and then irradiated with UV light for 2 hours under flow of argon. After filtration by a cannula system the solvent was evaporated form the yellow solution and orange crystals were under vacuum.

Examples 3 and 4

Synthesis of Complexes C3 and C4

General procedure

The Schlenck's tube (Pyrex glass) equipped with a magnetic stirrer and a condenser with oil valve was charged with 1.5 g (4.12 mmol) of $Fe_2(CO)_9$ and 4.46 g (41.2 mmol) of 1,5-cyclooctadiene or 2.77 g (24,72 mmol) of dimethyldivinylsilane or 3.89 g (16.48 mmol) of diphenyldivinylsilane and 50 mL of pentane. The mixture obtained was stirred overnight and then irradiated with UV light for 3 hours under flow of argon. The solution obtained was filtered off via a cannula system and then the solvent was evaporated from the yellow solution and orange oil was dried under vacuum.

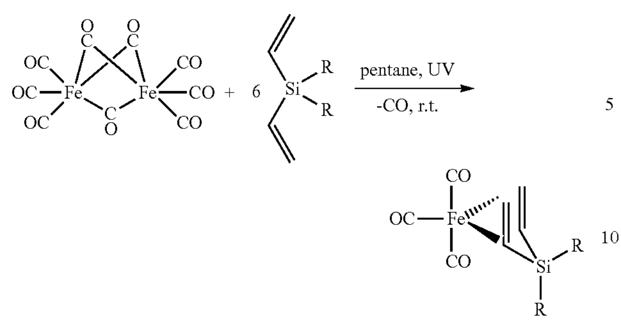

In the reaction formula above for the general procedure of examples 3 and 4, R is Me or Ph.

Example 3

Complex C3 where R=Me

$^1$H NMR (300 MHz, $C_6D_6$, 300 K) δ(ppm)=2.27 (bs); 1.93 (bm); 1.13 (bs) ($H_2C$═CH-coordinated); 0.44 (bs); −0.37 (bs) (6H, -Me);

$^{13}$C NMR (75.42 MHz, $C_6D_6$, 300 K) δ(ppm)=216.90 (CO); 57.58, 37.48 ($H_2C$═CH-coordinated); 2.68, −3.68 (-Me)

Example 4

Complex C4 where R=pH

$^1$H NMR (300 MHz, $C_6D_6$, 300 K) δ(ppm)=8.02 (m); 7.60 (m); 7.32 (m); 7.17 (m) (10H, Ph); 2.2 (dd, 1H, —HC═); 2.03 (d, 1H, $H_2C$=coordinated); 1.1 (d, 1H, $H_2C$=coordinated)

$^{13}$C NMR (75.42 MHz, $C_6D_6$, 300 K) δ(ppm)=216.05 (CO); 135.48, 134.09, 130.79, 130.03, 128.58, 128.24 (-Ph); 57.43, 34.30 ($H_2C$═CH— coordinated);

Synthesis of Iron(0) Complexes with Silicontrienes

Examples 5 and 6

Synthesis Complexes of the Type

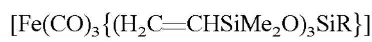

$[Fe(CO)_3\{(H_2C{=}CHSiMe_2O)_3SiR\}]$

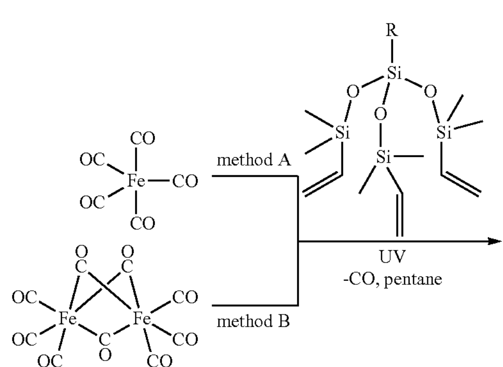

-continued

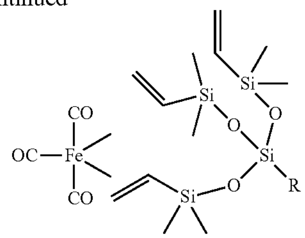

In the reaction formula above for the general procedure of examples 5 and 6, R is Me or Ph.

Method A

In the Schlenck's tube (Pyrex glass) equipped with magnetic stirrer, condenser with oil valve 6 mmol of appropriate organosilicone triene (($H_2C$═$CHSiMe_2O)_3SiR$), 1.18 g (6 mmol) $Fe(CO)_5$ and 40 mL of pentane were placed. The mixture obtained was irradiated with UV light for 2 hours under flow of argon. After filtration by a cannula system the solvent was evaporated from yellow solution and yellow oil was dried under vacuum.

Method B

In the Schlenck's tube (Pyrex glass) equipped with magnetic stirrer, condenser with oil valve 6 mmol of appropriate organosilicone triene (($H_2C$═$CHSiMe_2O)_3SiR$), 1.09 g (3 mmol) $Fe_2$ $(CO)_9$ and 40 mL of pentane were placed. The mixture obtained was mixed over-knight and then irradiated with UV light for 2 hours under flow of argon. After filtration by a cannula system the solvent was evaporated from yellow-orange solution and orange oil was dried under vacuum.

Example 5

Synthesis of Complex C5 where R=Me

Method A

$^1$H NMR (300 MHz, $C_6D_6$, 300 K) δ(ppm)=6.20 (two dd); 5.92 (dd); 5.78 (two dd) (free $H_2C$═CH—) 2.69 (d); 2.50 (d); 2.44 (m); 1.91 (dd) ($H_2C$═CH— coordinated); 0.30; 0.26; 0.23; 0.22; 0.17; 0.13 (s, Me-)

$^{13}$C NMR (75.42 MHz, $C_6D_6$, 300 K) δ(ppm)=211.83; 211.79 (CO); 139.26; 139.16; 132.18; 132.132.09 (free $H_2C$═CH—); 43.92; 43.71; 40.89; 40.79 ($H_2C$═CH— coordinated); 2.43; 1.94; 1.33; 0.33; 0.28; −1.83 (Me-)

Method B

$^1$H NMR (300 MHz, $C_6D_6$, 300 K) δ(ppm)=6.20 (two dd); 5.92 (dd); 5.81; 5.75 (two dd) (free $H_2C$═CH—) 2.60 (dd); 2.43 (dd); 1.99 (dd) ($H_2C$═CH— coordinated); 0.30; 0.27; 0.24; 0.22; 0.18; 0.14 (s, Me-)

$^{13}$C NMR (75.42 MHz, $C_6D_6$, 300 K) δ(ppm)=211.84; 211.79; 210.47 (CO); 139.27; 139.16; 132.18; 132.09 (free $H_2C$═CH—); 43.92; 43.72; 40.89; 40.79 ($H_2C$═CH-coordinated); 2.43; 1.95; 1.68; 1.33; 0.33; 0.28; −1.73; −1.83 (Me-)

Example 6

Synthesis of Complex C6 where R=pH

Method A

$^1$H NMR (300 MHz, $C_6D_6$, 300 K) δ(ppm)=7.80 (m); 7.22 (m) (Ph); 6.22 (dd); 5.92 (dd); 5.80; 5.78 (two dd) (free $H_2C$═CH—) 2.55 (dd); 2.42 (dd); 1.95 (dd) ($H_2C$═CH— coordinated); 0.31; 0.27; 0.25; 0.24; 0.21 (s, Me-)

$^{13}$C NMR (75.42 MHz, $C_6D_6$, 300 K) δ(ppm)=211.76; 211.73 (CO); 139.09; 139.03 (free $H_2C$═CH—); 135.27;

135.09; (Ph); 134.31; 134.30 (Ph) 132.40; 132.32 (free $H_2C{=}CH$—); 130.32; 130.23; 130.14 (Ph); 43.72; 43.57; 40.94; 40.87 ($H_2C{=}CH$— coordinated); 2.70; 2.62; 1.48; 1.34; 1.12; 0.39 (Me-)

Method B $^1H$ NMR (300 MHz, $C_6D_6$, 300 K) δ(ppm)=7.80 (m); 7.22 (m) (Ph); 6.22 (dd); 5.92 (dd); 5.80; 5.78 (two dd) (free $H_2C{=}CH$—) 2.66 (dd); 2.43 (dd); 1.90 (dd) ($H_2C{=}CH$— coordinated); 0.31; 0.27; 0.25; 0.24; 0.21 (s, Me-)

$^{13}C$ NMR (75.42 MHz, $C_6D_6$, 300 K) δ(ppm)=211.76; 211.73 (CO); 139.09; 139.03 (free $H_2C{=}CH$—); 135.27; 135.10; (Ph); 134.31; 134.30 (Ph) 132.40; 132.32 (free $H_2C{=}CH$—); 130.32; 130.23; 130.14 (Ph); 43.72; 43.56; 40.93; 40.87 ($H_2C{=}CH$— coordinated); 2.69; 2.62; 1.48; 1.34; 1.12; 0.39 (Me-)

Examples 7 and 8

Synthesis of C7 and C8

In the Schlenck's tube (Pyrex glass) equipped with magnetic stirrer, condenser with oil valve 6 mmol of appropriate organosilicone triene ($(H_2C{=}CH)_3SiR$) (R=Me in complex C7, and R=Ph in complex C8), 1.09 g (3 mmol) $Fe_2(CO)_9$ and 60 mL of pentane were placed. The mixture obtained was mixed over-knight and then irradiated with UV light for 2 hours under flow of argon. The solvent was evaporated from yellow-orange solution and orange oil was dried under vacuum.

1.3. Synthesis of Iron(0) Complexes with Organosilicone Tetraenes

Example 9

Synthesis of Complex C9

In the Schlenck's tube (Pyrex glass) equipped with magnetic stirrer, condenser with oil valve 0.41 (3 mmol) of $(H_2C{=}CH)_4Si$, 1.09 g (3 mmol) $Fe_2(CO)_9$ and 60 mL of pentane were placed. The mixture obtained was mixed over-knight and then irradiated with UV light for 2 hours under flow of argon. After filtration by a cannula system, the solvent was evaporated from yellow-orange solution and orange solid obtained was dried under vacuum.

Example 10

Synthesis of Complex C10

In the Schlenck's tube (Pyrex glass) equipped with magnetic stirrer, condenser with oil valve 3.1 g (9 mmol) of tetravinylcyclotetrasiloxane, 1.09 g (3 mmol) $Fe_2(CO)_9$ and 60 mL of pentane were placed. The mixture obtained was mixed over-knight and then irradiated with UV light for 2 hours under flow of argon. After filtration by a cannula system, the solvent was evaporated from yellow solution and yellow solid obtained was dried under vacuum.

Example 11

Synthesis of Complex C11

In the Schlenck's tube (Pyrex glass) equipped with magnetic stirrer, condenser with oil valve 3.07 g (9 mmol) of tetravinylcyclotetrasilazane, 1.09 g (3 mmol) $Fe_2(CO)_9$ and 60 mL of pentane were placed. The mixture obtained was mixed over-knight and then irradiated with UV light for 2 hours under flow of argon. After filtration by a cannula system, the solvent was evaporated from yellow solution and yellow solid obtained was dried under vacuum.

Synthesis of Iron(0) Complexes with Polyenes

Example 12

Synthesis of Complex C12

Method A

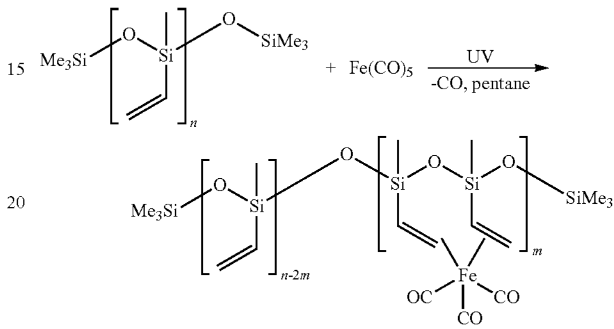

In the Schlenck's tube (Pyrex glass) equipped with magnetic stirrer condenser with oil valve 2.00 g of polyvinylsiloxane (homo-polymer), 0.363 (1.85 mmol) $Fe(CO)_5$ and 20 mL of pentane were placed. After filtration by a cannula system the mixture obtained was irradiated with UV light for 2 hours then the solvent was evaporated from yellow solution and yellow oil was dried under vacuum.

$^1H$ NMR (300 MHz, $C_6D_6$, 300 K) δ(ppm)=6.14 (m); 5.95 (m) (free $H_2C{=}CH$—); 3.08 (m); 2.63 (m); 1.93 (m) (coordinated vinyl groups); 0.36; 0.33; 0.28; 0.18 (-Me)

$^{13}C$ NMR (75.42 MHz, $C_6D_6$, 300 K) δ(ppm)=211.53 (m) (CO); 137.58; 39.23; 136.51 (m); 133.72 (m) (free vinyl groups) 40.54 (m, coordinated vinyl groups); 2.4, 1; 2.02; 1.40; −0.16; −0.54; −0.58 (-Me)

Method B

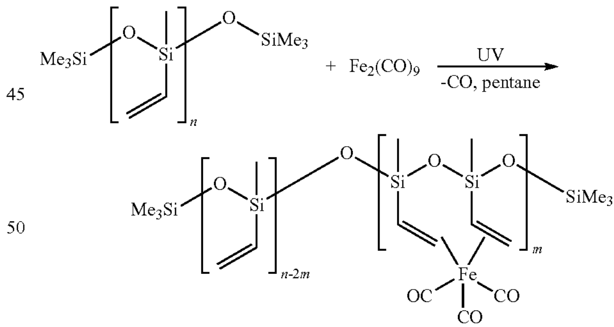

In the Schlenck's tube (Pyrex glass) equipped with magnetic stirrer, condenser with oil valve 2.00 g of polyvinylsiloxane (homo-polymer) 0.35 g (0.962 mmol) $Fe_2(CO)_9$ and 10 mL of pentane were placed. The mixture obtained was stirred over-night and then irradiated with UV light for 2 hours. After filtration by a cannula system the solvent was evaporated from yellow solution and yellow oil was dried under vacuum.

$^1H$ NMR (300 MHz, $C_6D_6$, 300 K) δ(ppm)=6.14 (m); 5.95 (m) (free $H_2C{=}CH$—); 2.64 (m); 1.93 (m) (coordinated vinyl groups); 0.37; 0.35; 0.33; 0.28; 0.19 (-Me)

$^{13}C$ NMR (75.42 MHz, $C_6D_6$, 300 K) δ(ppm)=211.53 (m) (CO); 137.59; 137.15; 136.51 (m); 133.72 (m) (free vinyl groups); 40.53; 40.20 (m, coordinated vinyl groups); 2.02; 1.40; −0.18; −0.54; −0.59; −0.78 (-Me)

In examples 13 to 16, [Fe] represents the concentration of one of the iron complexes prepared above in Examples 1 to 12 being used as a catalyst.

Example 13

Catalytic Activity of Iron Complexes in Transformation of Organosilicone Derivatives Model Reaction 1

A

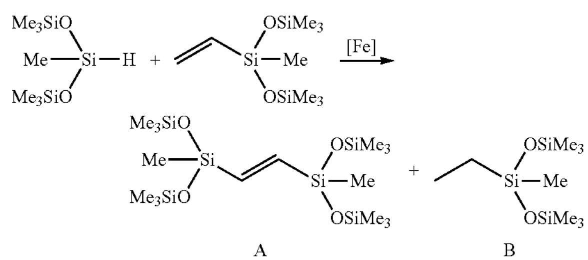

where [Fe] represents the concentration of one of the iron complex catalysts prepared above in Examples 1 to 12.

A hydrosilylation reaction according to model reaction 1 was performed by combining the SiH reactant and the Vi functional reactant in the model reaction above, with a catalyst prepared according to one of examples 1 to 12 above. The reaction was performed under argon. The amounts of SiH reactant, Vi functional reactant, and catalyst were sufficient to provide a molar ratio of [Si—H]:[SiCH═CH$_2$]:[Fe]=1:2:$10^{-2}$ or 1:2:$10^{-3}$. The reaction was performed at room temperature or at 100° C. The catalyst used and the amount of catalyst, the reaction time, the conversion, and the yield of desired product A in the model reaction above (selectivity) are shown below in Table 13-1. In Table 13-1, a denotes the reaction was performed at room temperature; all other runs were performed at 100° C., and b denotes that the mole ratio [Si—H]:[SiCH═CH$_2$]:[Fe]=1:2:$10^{-3}$; all other runs were at a molar ratio of [Si—H]:[SiCH═CH$_2$]:[Fe]=1:2:$10^{-2}$.

TABLE 13-1

Catalytic performance of iron(0) complexes with vinylorganosilicon ligands

| Catalyst | Time [hours] | Conversion of Si—H(Vi—Si) [%] | Yield of A [%] |
|---|---|---|---|
| C1 | 1 | 39(40) | 39[a] |
| | 24 | 59(61) | 59[a] |
| | 72 | 76(77) | 76[a] |
| | 1 | 88(89) | 88 |
| | 2 | 99(99) | 99 |
| | 1 | 6(7) | 6[b] |
| | 24 | 9(11) | 9[b] |
| C12 | 1 | 57(58) | 57[a] |
| | 24 | 83(85) | 83[a] |
| | 72 | 85(87) | 85[a] |
| | 1 | 97(98) | 97 |
| | 1 | 7(8) | 7[b] |
| | 24 | 12(14) | 12[b] |
| C5 | 1 | 80(82) | 80 |
| | 20 | 100(100) | 100 |
| | 1 | 23(25) | 23[b] |
| | 20 | 32(33) | 22[b] |

TABLE 13-1-continued

Catalytic performance of iron(0) complexes with vinylorganosilicon ligands

| Catalyst | Time [hours] | Conversion of Si—H(Vi—Si) [%] | Yield of A [%] |
|---|---|---|---|
| C6 | 1 | 75(77) | 75 |
| | 20 | 100(100) | 100 |
| | 1 | 14(15) | 14[b] |
| | 24 | 83(85) | 83[b] |

Screening of steric demand influence of organosilicon reagents on selectivity of iron(0) complexes was performed using model reaction 2.

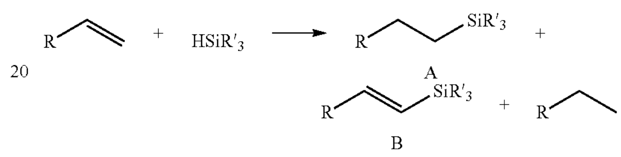

A hydrosilylation reaction was performed by combining the Vi functional reactant and the SiH reactant and in the model reaction above, with a catalyst prepared according to one of examples 1 to 12 above. Amounts of each reactant and catalyst were sufficient to provide a mole ratio [RCH═CH$_2$]:[HSiR'$_3$]:[Fe]=1:1:$10^{-2}$. The reaction was performed under argon at 80° C.

The catalyst, the amount of catalyst, the reaction time, the conversion, and the yield of desired product A in the model reaction above (selectivity) are shown below in Table 13-2.

TABLE 13-2

| Catalyst | R | R'$_3$ | Time [hours] | Conversion of Si—H [%] | Yield A(B) [%] |
|---|---|---|---|---|---|
| C1 | SiMe$_2$(OSiMe$_3$) | Me$_2$(OSiMe$_3$) | 1 | 42 | 0(42) |
| | | | 24 | 50 | 0(50) |
| | Si(OSiMe$_3$)$_3$ | Me$_2$(OSiMe$_3$) | 1 | 43 | 0(43) |
| | | | 24 | 44 | 0(44) |
| | SiMe(OSiMe$_3$)$_2$ | Me$_2$(OSiMe$_3$) | 1 | 55 | 0(55) |
| | | | 24 | 63 | 0(63) |
| C3 | SiMe$_2$(OSiMe$_3$) | Me$_2$(OSiMe$_3$) | 1 | 40 | 0(40) |
| | | | 24 | 56 | 0(56) |
| | Si(OSiMe$_3$)$_3$ | Me$_2$(OSiMe$_3$) | 1 | 45 | 0(45) |
| | | | 24 | 64 | 0(64) |
| | SiMe(OSiMe$_3$)$_2$ | Me$_2$(OSiMe$_3$) | 1 | 62 | 5(57) |
| | | | 24 | 63 | 8(55) |
| C4 | SiMe$_2$(OSiMe$_3$) | Me$_2$(OSiMe$_3$) | 1 | 43 | 0(43) |
| | | | 24 | 56 | 0(56) |
| | Si(OSiMe$_3$)$_3$ | Me$_2$(OSiMe$_3$) | 1 | 25 | 0(25) |
| | | | 24 | 35 | 0(35) |
| | SiMe(OSiMe$_3$)$_2$ | Me$_2$(OSiMe$_3$) | 1 | 32 | 0(32) |
| | | | 24 | 35 | 0(35) |
| C1 | SiMe$_2$(OSiMe$_3$) | Me$_2$(OSiMe$_3$) | 1 | 86 | 0(86) |
| | | | 24 | 87 | 0(87) |
| | Si(OSiMe$_3$)$_3$ | Me$_2$(OSiMe$_3$) | 1 | 34 | 0(34) |
| | | | 24 | 36 | 0(36) |
| | SiMe(OSiMe$_3$)$_2$ | Me$_2$(OSiMe$_3$) | 1 | 77 | 0(77) |
| | | | 24 | 96 | 0(96) |
| C3 | SiMe$_2$(OSiMe$_3$) | Me$_2$(OSiMe$_3$) | 1 | 85 | 0(85) |
| | | | 24 | 100 | 0(100) |
| | Si(OSiMe$_3$)$_3$ | Me$_2$(OSiMe$_3$) | 1 | 26 | 0(26) |
| | | | 24 | 27 | 0(27) |
| | Me(OSiMe$_3$)$_2$ | Me$_2$(OSiMe$_3$) | 1 | 72 | 14(58) |
| | | | 24 | 100 | 20(80) |
| C4 | SiMe$_2$(OSiMe$_3$) | Me$_2$(OSiMe$_3$) | 1 | 56 | 0(56) |
| | | | 24 | 57 | 0(57) |

TABLE 13-2-continued

| Catalyst | R | R'$_3$ | Time [hours] | Conversion of Si—H [%] | Yield A(B) [%] |
|---|---|---|---|---|---|
| | $Si(OSiMe_3)_3$ | $Me_2(OSiMe_3)$ | 1 | 40 | 0(40) |
| | | | 24 | 42 | 0(42) |
| | $SiMe(OSiMe_3)_2$ | $Me_2(OSiMe_3)$ | 1 | 35 | 0(35) |
| | | | 24 | 37 | 0(37) |
| | $SiMe(OSiMe_3)_2$ | $Me(OSiMe_3)_2$ | 1 | 82 | 0(82) |
| | | | 24 | 85 | 0(85) |

$[Fe(CO)_3(diene)]$ catalyzed reaction of olefins with trisubstituted silanes was evaluated by reacting the Vi functional reactant and the SiH reactant and in model reaction 2 above, with a catalyst prepared according to one of examples 1 to 12 above. Table 13-3 shows group R of the Vi functional reactant, group R'$_3$ of the SiH functional compound of formula $HSiR'_3$, reaction temperature, reaction time, yield, and selectivity. The reaction conditions were as follows. Molar ratio was $[HSiR'_3]:[Fe]:=1:10^{-2}$, unless otherwise indicated; a denotes molar ratio $[RCH{=}CH_2]:[HSiR'_3]=1:1$; b denotes molar ratio $[RCH{=}CH_2]:[HSiR'_3]=2:1$; and c denotes molar ratio $[RCH{=}CH_2]:[HSiR'_3]=1:1.1$ in table 13-3, below.

TABLE 13-3

$[Fe(CO)_3(diene)]$ catalyzed reaction of olefins with trisubstituted silanes

| Cat. | R | R'$_3$ | Temp. [° C.] | Time [hours] | Conversion of Si—H [%] | Yield A(B) [%] |
|---|---|---|---|---|---|---|
| C1 | Ph[a] | $Et_3$ | 100 | 1 | 41 | 0(41) |
| | | | | 24 | 45 | 0(45) |
| | Ph[b] | $Et_3$ | RT | 1 | 67 | 0(67) |
| | | | | 7 | 83 | 0(83) |
| | | | | 24 | 85 | 0(85) |
| | Ph[a] | $Me_2Ph$ | 100 | 1 | 39 | 11(28) |
| | | | | 24 | 39 | 11(28) |
| | Ph[a] | $Me_2Ph$ | 60 | 1 | 39 | 13(26) |
| | | | | 24 | 41 | 13(28) |
| | | | | 48 | 45 | 13(32) |
| | Ph[a] | $Me(OSiMe_3)_2$ | 100 | 1 | 51 | 4(47) |
| | | | | 24 | 54 | 4(50) |
| | Ph[a] | $Me(OSiMe_3)_2$ | 60 | 1 | 61 | 3(58) |
| | | | | 24 | 67 | 5(62) |
| | | | | 48 | 69 | 5(64) |
| | Ph[b] | $Me(OSiMe_3)_2$ | 60 | 1 | 62 | 2(60) |
| | | | | 24 | 80 | 2(78) |
| | Ph[a] | $(OEt)_3$ | 100 | 1 | 1 | 1 |
| | | | | 24 | 25 | 24 |
| | $C_6H_{13}$[a] | $Et_3$ | 60 | 1 | hydrosilylation + dehydrogenative | |
| | | | | 24 | silylation products | |
| | | | | 48 | (isomers) | |
| | $C_6H_{13}$[a] | $Me_2Ph$ | 60 | 1 | 11 | 7(4) |
| | | | | 24 | 28 | 15(12) |
| | | | | 48 | 31 | 17(14) |
| | $C_6H_{13}$[a] | $Me(OSiMe_3)_2$ | 60 | 24 | 15 | 2(13) |
| | | | | 48 | 24 | 3(19) |
| | $SiMe(OSiMe_3)_2$[b] | $(OEt)_3$ | 60 | | unselective reaction | |
| | $Si(OEt)_3$[b] | $Me_2Ph$ | 60 | 1 | 48 | 6(42) |
| | | | | 24 | 60 | 13(47) |
| | $Si(OEt)_3$[b] | $Et_3$ | 60 | 1 | 40 | 0(40) |
| | | | | 24 | 53 | 0(53) |
| | | | | 48 | 60 | 0(60) |
| | $Si(OEt)_3$[b] | $Me(OSiMe_3)_2$ | 60 | 1 | 49 | 7(42) |
| | | | | 24 | 53 | 7(46) |
| | | | | 48 | 64 | 10(54) |
| C3 | Ph[b] | $Et_3$ | 80 | 1 | 28 | 0(28) |
| | | | | 24 | 30 | 0(30) |
| | Ph[b] | $Me_2Ph$ | 80 | 1 | 35 | 0(35) |
| | | | | 24 | 40 | 0(40) |
| | Ph[b] | $Me(OSiMe_3)_2$ | 80 | 1 | 38 | 0(38) |
| | | | | 24 | 41 | 0(41) |
| | Ph[c] | $Me_2(OEt)$ | 80 | 1 | 0 | 0(0) |
| | | | | 24 | 0 | 0(0) |
| | $SiMe(OSiMe_3)_2$ | $Me_2(OEt)$ | 80 | 1 | 0 | 0(0) |
| | | | | 24 | 0 | 0(0) |
| C4 | Ph[b] | $Et_3$ | 80 | 1 | 31 | 0(31) |
| | | | | 24 | 32 | 0(32) |
| | Ph[b]b | $Me_2Ph$ | 80 | 1 | 22 | 0(22) |
| | | | | 24 | 24 | 0(24) |
| | Ph[b] | $Me(OSiMe_3)_2$ | 80 | 1 | 42 | 0(42) |
| | | | | 24 | 43 | 0(43) |
| | Ph[c] | $Me_2(OEt)$ | 80 | 1 | 0 | 0(0) |
| | | | | 24 | 0 | 0(0) |

Catalytic activity of $[Fe(CO)_3(diene)]$ in hydrosilylation of vinyl derivatives was evaluated by reacting the Vi functional reactant and the SiH reactant and in model reaction 2 above, with a catalyst prepared according to one of examples 1 to 12 above. Table 13-4 shows group R of the Vi functional reactant, group $R'_3$ of the SiH functional compound of formula $HSiR'_3$, reaction temperature, reaction time, yield, and selectivity. The reaction was performed under argon using a catalyst prepared in examples 1-12. Molar ratio was $[RCH{=}CH_2]:[HSiR'_3]:[Fe]=1:1:10^{-2}$.

TABLE 13-4

Catalytic activity of $[Fe(CO)_3(diene)]$ in hydrosilylation of vinyl derivatives under mild conditions.

| Cat. | R | R'$_3$ | Temp. [° C.] | Time [hours] | Conversion of Si—H [%] | Yield A(B) [%] |
|---|---|---|---|---|---|---|
| C3 | Ph | $Me_2Ph$ | 0 | 1 | 0 | 0 |
| | | | | 24 | 0 | 0 |
| | Ph | $Me_2Ph$ | 10 | 1 | 0 | 0 |
| | | | | 24 | 63 | 12(51) |
| | $SiMe(OSiMe_3)_2$ | $Me(OSiMe_3)_2$ | 0 | 1 | 0 | 0 |
| | | | | 24 | 0 | 0 |
| | $SiMe(OSiMe_3)_2$ | $Me(OSiMe_3)_2$ | 10 | 1 | 14 | 0(14) |
| | | | | 24 | 27 | 0(27) |
| C4 | Ph | $Me_2Ph$ | 0 | 1 | 0 | 0 |
| | | | | 24 | 0 | 0 |
| | Ph | $Me_2Ph$ | 10 | 1 | 0 | 0 |
| | | | | 24 | 0 | 0 |
| | $SiMe(OSiMe_3)_2$ | $Me(OSiMe_3)_2$ | 0 | 1 | 0 | 0 |
| | | | | 24 | 0 | 0 |
| | $SiMe(OSiMe_3)_2$ | $Me(OSiMe_3)_2$ | 10 | 1 | 0 | 0 |
| | | | | 24 | 0 | 0 |
| | | | | 48 | 46 | 0(46) |

TABLE 13-4-continued

Catalytic activity of $[Fe(CO)_3(diene)]$ in hydrosilylation of vinyl derivatives under mild conditions.

| Cat. | R | R'$_3$ | Temp. [° C.] | Time [hours] | Conversion of Si—H [%] | Yield A(B) [%] |
|---|---|---|---|---|---|---|
| C1 | Ph | $Me_2Ph$ | 0 | 1 | 40 | 34(6) |
| | | | | 24 | 83 | 75(8) |
| | Ph | $Me_2Ph$ | -15 | 1 | 11 | 9(2) |
| | | | | 24 | 56 | 51(5) |
| | | | | 48 | 68 | 60(8) |
| | Ph | $Me_2Ph$ | 10 | 1 | 0 | 0 |
| | | | | 24 | 61 | 61(0) |
| | | | | 48 | 77 | 77(0) |
| | $SiMe(OSiMe_3)_2$ | $Me(OSiMe_3)_2$ | 0 | 1 | 0 | 0 |
| | | | | 24 | 0 | 0 |
| | $SiMe(OSiMe_3)_2$ | $Me(OSiMe_3)_2$ | 10 | 1 | 0 | 0 |
| | | | | 24 | 22 | 0(22) |
| | | | | 48 | 33 | 0(33) |
| | $C_6H_{13}$ | $Et_3$ | −15 | 1 | 53 | 25(28) |
| | | | | 24 | 57 | 26(31) |
| | $C_6H_{13}$ | $Me_2Ph$ | −15 | 24 | 31 | 11(20) |
| | | | | 48 | 34 | 11(22) |

Catalytic activity of complexes C2 and C8 was evaluated by reacting the Vi functional reactant and the SiH reactant and in model reaction 2 above, with a catalyst prepared according to one of examples 1 to 12 above. Table 13-5 shows group R of the Vi functional reactant, group $R'_3$ of the SiH functional compound of formula $HSiR'_3$, reaction temperature, reaction time, yield, and selectivity. The reaction was performed under argon using a catalyst prepared in examples 1-12. Molar ratio was $[RCH{=}CH_2]:[HSiR'_3]:[Fe]=1:1:10^{-2}$.

TABLE 13-5

| Cat. | R | R'$_3$ | Temp. [° C.] | Time [hours] | Conversion of Si—H [%] | Yield A(B) [%] |
|---|---|---|---|---|---|---|
| C2 | $Me(OSiMe_3)_2$ | $Me(OSiMe_3)_2$ | 80 | 1 | 48 | 0(48) |
| | | | | 24 | 100 | 0(100) |
| | $SiMe_2(OSiMe_3)$ | $Me_2(OSiMe_3)$ | 80 | 1 | 96 | 0(96) |
| | | | | 24 | 100 | 0(100) |
| | $SiMe_2(OSiMe_3)$ | $Me(OSiMe_3)_2$ | 80 | 1 | 42 | 0(42) |
| | | | | 24 | 43 | 0(43) |
| | $Si(OSiMe_3)_3$ | $Me(OSiMe_3)_2$ | 80 | 1 | 6 | 0(6) |
| | | | | 24 | 10 | 0(10) |
| | Ph | $Et_3$ | 80 | 1 | 29 | 0(29) |
| | | | | 24 | 30 | 0(30) |
| | Ph | $Me_2Ph$ | 80 | 1 | 53 | 0(53) |
| | | | | 24 | 61 | 0(61) |
| | Ph | $Me(OSiMe_3)_2$ | 80 | 1 | 30 | 0(30) |
| | | | | 24 | 33 | 0(33) |
| C8 | Ph | $Et_3$ | 80 | 1 | 61 | 0(61) |
| | | | | 24 | 84 | 0(84) |
| | Ph | $Me_2Ph$ | 80 | 1 | 87 | 0(87) |
| | | | | 24 | 88 | 0(88) |
| | Ph | $Me(OSiMe_3)_2$ | 80 | 1 | 100 | 0(100) |
| | $Me(OSiMe_3)_2$ | $Me(OSiMe_3)_2$ | 80 | 1 | 100 | 0(100) |
| | $SiMe_2(OSiMe_3)$ | $Me_2(OSiMe_3)$ | 80 | 1 | 100 | 0(100) |
| | $SiMe_2(OSiMe_3)$ | $Me(OSiMe_3)_2$ | 80 | 1 | 100 | 36(64) |

Catalytic activity of complex C7 was evaluated by reacting the Vi functional reactant and the SiH reactant and in model reaction 2 above, with a catalyst prepared according to one of examples 1 to 12 above. Table 13-6 shows group R of the Vi functional reactant, group $R'_3$ of the SiH functional compound of formula $HSiR'_3$, reaction temperature, reaction time, yield, and selectivity. The reaction was performed under argon using a catalyst prepared in examples 1-12. Molar ratio was $[RCH{=}CH_2]:[HSiR'_3]:[Fe]=2:1:10^{-2}$.

TABLE 13-6

| R | R'3 | Temp. [° C.] | Time [hours] | Conversion of Si—H [%] | Yield A(B) [%] |
|---|---|---|---|---|---|
| Ph | $Et_3$ | 80 | 1 | 72 | 0(72) |
| | | | 24 | 91 | 0(91) |
| Ph | $Me_2Ph$ | 80 | 1 | 60 | 0(60) |
| | | | 24 | 63 | 0(63) |
| Ph | $Me(OSiMe_3)_2$ | 80 | 1 | 100 | 0(100) |
| $Me(OSiMe_3)_2$ | $Me(OSiMe_3)_2$ | 80 | 1 | 100 | 0(100) |
| $SiMe_2(OSiMe_3)$ | $Me_2(OSiMe_3)$ | 80 | 1 | 100 | 0(100) |
| $SiMe_2(OSiMe_3)$ | $Me(OSiMe_3)_2$ | 80 | 1 | 100 | 30(70) |
| $Si(OSiMe_3)_3$ | $Me(OSiMe3)_2$ | 80 | 1 | 100 | 6(94) |

Catalytic activity of complex C7 was evaluated by reacting the Vi functional reactant and the SiH reactant and in model reaction 2 above, with a catalyst prepared according to one of examples 1 to 12 above. Table 13-7 shows group R of the Vi functional reactant, group $R'_3$ of the SiH functional compound of formula $HSiR'_3$, reaction temperature, reaction time, yield, and selectivity. The reaction was performed under argon using a catalyst prepared in examples 1-12. Molar ratio was $[RCH{=}CH_2]:[HSiR'_3]:[Fe]=1:1:10^{-2}$.

TABLE 13-7

| R | R'3 | Temp. [° C.] | Time [hours] | Conversion of Si—H [%] | Yield A(B) [%] |
|---|---|---|---|---|---|
| $SiMe(OSiMe_3)_2$ | $Me(OSiMe_3)_2$ | 80 | 1 | 2 | 0(2) |
| | | | 24 | 8 | 0(8) |
| $SiMe_2(OSiMe_3)$ | $Me_2(OSiMe_3)$ | 80 | 1 | 12 | 0(12) |
| | | | 24 | 30 | 0(30) |

Catalytic activity of complexes C9 and C10 was evaluated by reacting the Vi functional reactant and the SiH reactant and in model reaction 2 above, with a catalyst prepared according to one of examples 1 to 12 above. Table 13-8 shows group R of the Vi functional reactant, group $R'_3$ of the SiH functional compound of formula $HSiR'_3$, reaction temperature, reaction time, yield, and selectivity. The reaction was performed under argon using a catalyst prepared in examples 1-12. Molar ratio was $[RCH{=}CH_2]:[HSiR'_3]:[Fe]=2:1:10^{-2}$.

TABLE 13-8

| Cat. | R | R'3 | Temp. [° C.] | Time [hours] | Conversion of Si—H [%] | Yield A(B) [%] |
|---|---|---|---|---|---|---|
| C10 | $SiMe(OSiMe_3)_2$ | $Me(OSiMe_3)_2$ | 80 | 1 | 85 | 0(85) |
| | | | | 24 | 97 | 0(97) |
| | $SiMe_2(OSiMe_3)$ | $Me_2(OSiMe_3)$ | 80 | 1 | 56 | 0(56) |
| | | | | 24 | 71 | 0(71) |

TABLE 13-8-continued

| Cat. | R | R'3 | Temp. [° C.] | Time [hours] | Conversion of Si—H [%] | Yield A(B) [%] |
|---|---|---|---|---|---|---|
| | $SiMe_2(OSiMe_3)$ | $Me(OSiMe_3)_2$ | 80 | 1 | 55 | 0(55) |
| | | | | 24 | 70 | 0(70) |
| | $Si(OSiMe_3)_3$ | $Me(OSiMe_3)_2$ | 80 | 1 | 55 | 22(33) |
| | | | | 24 | 100 | ? |
| | Ph | $Et_3$ | 80 | 1 | 56 | 0(56) |
| | | | | 24 | 66 | 0(66) |
| | Ph | $Me_2Ph$ | 80 | 1 | 61 | 0(61) |
| | | | | 24 | 70 | 0(70) |
| | Ph | $Me(OSiMe_3)_2$ | 80 | 1 | 100 | 0(100) |
| C9 | $SiMe(OSiMe_3)_2$ | $Me(OSiMe_3)_2$ | 80 | 1 | 55 | 0(55) |
| | | | | 24 | 58 | 0(58) |
| | $SiMe_2(OSiMe_3)$ | $Me_2(OSiMe_3)$ | 80 | 1 | 98 | 0(98) |
| | | | | 24 | 100 | 0(100) |
| | $SiMe_2(OSiMe_3)$ | $Me(OSiMe_3)_2$ | 80 | 1 | 90 | 0(90) |
| | | | | 24 | 100 | 0(100) |
| | $Si(OSiMe_3)_3$ | $Me(OSiMe_3)_2$ | | 1 | 66 | 6(60) |
| | | | | 24 | 70 | 12(58) |
| | Ph | $Et_3$ | 80 | 1 | 42 | 0(42) |
| | | | | 24 | 65 | 0(65) |
| | Ph | $Me_2Ph$ | 80 | 1 | 43 | 0(43) |
| | | | | 24 | 53 | 0(53) |
| | Ph | $Me(OSiMe_3)_2$ | 80 | 1 | 57 | 0(57) |
| | | | | 24 | 66 | 0(66) |

Catalytic activity of complexes C1, C3, and C4 was evaluated by reacting the Vi functional reactant and the SiH reactant and in model reaction 2 above, with a catalyst prepared according to one of examples 1 to 12 above. Table 13-9 shows group R of the Vi functional reactant, group $R'_3$ of the SiH functional compound of formula $HSiR'_3$, yield, and selectivity. The reaction was performed under argon using a catalyst prepared in examples 1-12. Molar ratio was $[RCH{=}CH_2]:[HSiR'_3]:[Fe]=2:1:10^{-2}$. The reaction was performed by UV irradiation of the sample for a reaction time=30 min. at a temperature=40° C.,

TABLE 13-9

UV initiated reactions of olefins with trisubstituted silanes catalyzed by Fe(0) complexes.

| Catalyst | R | R'3 | Conversion of Si—H [%] | Yield A(B) [%] |
|---|---|---|---|---|
| C1 | Ph | $Et_3$ | 41 | 0(41) |
| | | $Me_2Ph$ | 0 | 0(0) |
| | | $Me(OSiMe_3)_2$ | 60 | 0(60) |
| | $SiMe(OSiMe_3)_2$ | $Me(OSiMe_3)_2$ | 91 | 0(91) |
| C3 | Ph | $Et_3$ | 44 | 0(44) |
| | | $Me_2Ph$ | 53 | 11(42) |
| | | $Me(OSiMe_3)_2$ | 43 | 0(43) |
| | $SiMe(OSiMe_3)_2$ | $Me(OSiMe_3)_2$ | 83 | 0(83) |
| C4 | Ph | $Et_3$ | 24 | 0(24) |
| | | $Me_2Ph$ | 22 | 0(22) |
| | | $Me(OSiMe_3)_2$ | 44 | 0(44) |
| | $SiMe(OSiMe_3)_2$ | $Me(OSiMe_3)_2$ | 98 | 0(98) |

Example 14

Iron(0) Catalyzed Reaction of Ethylene with Trisubstituted Silanes

Model Reaction 3

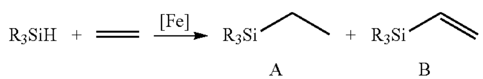

where [Fe] represents the concentration of one of the iron complex catalysts prepared above in Examples 1 to 12.

A hydrosilylation reaction according to model reaction 3 was performed by combining the SiH reactant and ethylene in the model reaction above, with a catalyst prepared according to one of examples 1 to 12 above. The reaction was performed under argon. The amounts of SiH reactant, Vi functional reactant, and catalyst were sufficient to provide a molar ratio of $[R_3SiH]:[Fe]=1:10^{-2}$. The reaction was performed at a pressure of ethylene of 14 bar. The catalyst used, the reaction temperature, the reaction time, the conversion, and the yield of desired product A in the model reaction above (selectivity) are shown below in Table 14.

TABLE 14

Iron(0) catalyzed hydrosilylation of ethylene

| Catalyst | R | Temp. [° C.] | Time [hours] | Conversion of Si—H [%] | Yield A(B) [%] |
|---|---|---|---|---|---|
| C1 | $HSiMe_2Ph$ | 80 | 18 | 100 | 69(31) |
| | $SiMe(OSiMe_3)_2$ | 60 | 18 | 0 | 0 |
| C3 | $HSiMe_2Ph$ | 80 | 18 | 100 | 74(26) |
| | $SiMe(OSiMe_3)_2$ | 60 | 18 | 0 | 0 |
| C4 | $HSiMe_2Ph$ | 60 | 18 | 80 | 73(7) |
| | | 80 | 18 | 100 | 70(30) |

Example 15

Hydrosilylation of internal alkynes

Hydrosilylation of Diphenylacetylene

Model Reaction 4

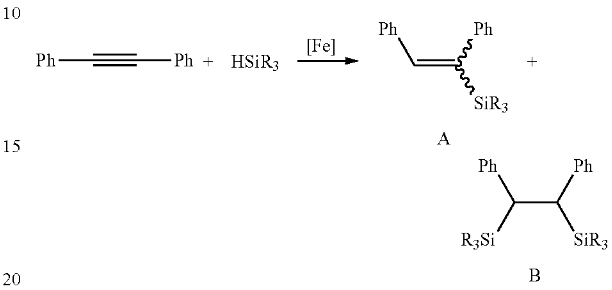

where [Fe] represents the concentration of one of the iron complex catalysts prepared above in Examples 1 to 12.

A hydrosilylation reaction according to model reaction 4 was performed by combining the SiH reactant and diphenylacetylene in the model reaction above, with a catalyst prepared according to one of examples 1 to 12 above. The samples were prepared under argon. The amounts of SiH reactant and diphenylacetylene were sufficient to provide a molar ratio shown in Table 15-1. The reaction was performed in toluene solvent. The molar amount of iron from the catalyst was $10^{-2}$. The catalyst used, definition of $R'_3$ in the SiH reactant, molar ratio of alkyne: $HSiR'_3$, the reaction temperature, the reaction time, the conversion, and the yield of desired product A in the model reaction above (selectivity) are shown below in Table 15-1. In Table 15-1, i denotes after 1 hour $HSiR_3$ was added up to 1:1 molar ratio, $[Fe]=10^{-2}$, and ii denotes catalyst was added.

TABLE 15-1

Iron(0) catalyzed hydrosilylation of diphenylacetylene

| Cat. | $R_3$ | Alkyne:$HSiR'_3$ | Temp. [° C.] | Time [hours] | Conversion of Si—H [%] | Yield of A(E/Z) [%] | Yield of B [%] |
|---|---|---|---|---|---|---|---|
| C1 | $Et_3$ | 1:1 | 100 | 1 | 78 | 78 | 0 |
| | | | | 24 | 90 | 90 | 0 |
| | | $2:1^{i}$ | 100 | 1 | 63 | 63 | 0 |
| | | | | 4 | 78 | 78 | 0 |
| | | | | 24 | 94 | 94 | 0 |
| | $Me_2Ph$ | 1:1 | 60 | 1 | 0 | 0 | 0 |
| | | | | 24 | 33 | 24(5/1) | 9 |
| | | | | 48 | 49 | 37(5/1) | 12 |
| | | 1.1:1 | 80 | 2 | 100 | 84(17/1) | 16 |
| | | 1:2.1 | 80 | 1 | 21 | 13(6/1) | 8 |
| | | | | 72 | 24 | 15(7/1) | 9 |
| | | 1:1 | 100 | 1 | 76 | 76(8/1) | 0 |
| | | | | 4 | 77 | 62(9/1) | 17 |
| | | | | 24 | 79 | 62(10/1) | 17 |
| | | 1.3:1 | 100 | 1 | 100 | 90(15/1) | 10 |
| | | $2:1^{i}$ | 100 | 1 | 100 | 100(15/1) | 0 |
| | | | | 24 | 98 | 90(14/1) | 8 |
| | | 1:2.1 | 100 | 2 | 37 | 21(6/1) | 17 |
| | | | | 24 | 37 | 21(7/1) | 16 |
| | | | | $30^{ii}$ | 37 | 37 | 22 |
| | $Me(OSiMe_3)_2$ | 1:1 | 60 | 1 | 6 | 6 | 0 |
| | | | | 24 | 85 | 75(11/1) | 10 |
| | | | | 48 | 99 | 88(11/1) | 11 |

TABLE 15-1-continued

| Iron(0) catalyzed hydrosilylation of diphenylacetylene | | | | | | | |
|---|---|---|---|---|---|---|---|
| Cat. | $R_3$ | Alkyne:HSiR'$_3$ | Temp. [° C.] | Time [hours] | Conversion of Si—H [%] | Yield of A(E/Z) [%] | Yield of B [%] |
| | | 1.05:1 | 80 | 1 | 34 | 34 | 0 |
| | | | | 4 | 45 | 42 | 3 |
| | | | | 24 | 47 | 42(13/1) | 5 |
| | | 1.2:1 | 80 | 1 | 100 | 100(11/1) | 0 |
| | | 1:1 | 100 | 3 | 100 | 95(11/1) | 5 |
| C3 | $Et_3$ | 1:1 | 80 | 1 | 54 | 54 | 0 |
| | | | | 24 | 55 | 55 | 0 |
| | $Me_2Ph$ | 1.1:1 | 80 | 1 | 100 | 80 | 20 |
| | | | | 24 | — | — | |
| | $Me(OSiMe_3)_2$ | 1.2:1 | 80 | 1 | 95 | 88 | 7 |
| | | | | 24 | 96 | 90 | 6 |
| C4 | $Et_3$ | 1:1 | 80 | 1 | 31 | 31 | 0 |
| | | | | 24 | 36 | 36 | 0 |
| | $Me_2Ph$ | 1.1:1 | 80 | 1 | 44 | 33 | 11 |
| | | | | 24 | 46 | 36 | 10 |
| | $Me(OSiMe_3)_2$ | 1.2:1 | 80 | 1 | 32 | 30 | 2 |
| | | | | 24 | 32 | 30 | 2 |

Model Reaction 5

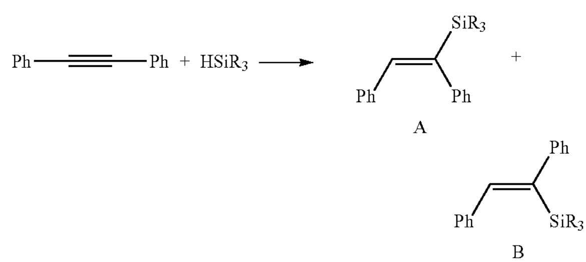

A hydrosilylation reaction according to model reaction 5 was performed by combining $HSiMe_2(OSiMe_3)$ (i.e., the SiH functional species shown above where $R^3$ is $Me_2(OSiMe_3)$) and diphenylacetylene in the model reaction above, with a catalyst prepared according to one of examples 1 to 12 above. The samples were prepared under argon. The amounts of $HSiMe_2(OSiMe_3)$, diphenylacetylene, and catalyst were sufficient to provide the molar ratios $[HSiR'_3]:[Fe]=1:10^{-2}$ and $[PhCCPh]:[HSiR_3]=1:1$. The catalyst used, the reaction temperature, the reaction time, the conversion, and the selectivity are shown below in Table 15-2. Table 15-2.

| Cat | Temp. [° C.] | Time [hours] | Conversion of Si—H [%] | Yield A(B) [%] |
|---|---|---|---|---|
| C1 | 80 | 1 | 82 | 57(12) |
| | | 24 | 86 | 69(17) |
| C3 | 80 | 1 | 71 | 55(16) |
| | | 24 | 73 | 57(16) |
| C4 | 80 | 1 | 66 | 54(12) |
| | | 24 | 72 | 60(12) |
| | 80 | 1 | 68 | 54(14) |
| | | 24 | 97 | 79(18) |
| C8 | −10 | 1 | 0 | 0 |
| | | 24 | 0 | 0 |
| | RT | 1 | 0 | 0 |
| | | 24 | 0 | 0 |
| | 80 | 1 | 58 | 45(13) |
| | | 24 | 96 | 78(19) |

A hydrosilylation reaction according to model reaction 5 was performed by combining the SiH functional species shown above where $R^3$ is shown in Table 15-3, below, and diphenylacetylene, with a catalyst prepared according to one of examples 1 to 12 above. The samples were prepared under argon. The amounts of SiH functional reactant, diphenylacetylene, and catalyst were sufficient to provide the molar ratios Reaction conditions: $[HSiR_3]:[Fe]=1:10^{-2}$ and $[RCH{=}CH_2]:[HSiR_3]=2:1$. The catalyst used, the reaction temperature, the reaction time, the conversion, and the selectivity are shown below in Table 15-3.

TABLE 15-3

| Catalyst | $R_3$ | Temp. [° C.] | Time [hours] | Conversion of Si—H [%] | Yield A(B) [%] |
|---|---|---|---|---|---|
| C10 | $Et_3$ | 80 | 1 | 12 | 12(0) |
| | | | 24 | 13 | 13(0) |
| | $Me_2Ph$ | 80 | 1 | 23 | 23(0) |
| | | | 24 | 24 | 24(0) |
| | $Me_2(OSiMe_3)$ | 80 | 1 | 53 | 41(12) |
| | | | 24 | 61 | 48(13) |
| | $Me(OSiMe_3)_2$ | 80 | 1 | 34 | 34(0) |
| | | | 24 | 54 | 54(0) |
| C7 | $Et_3$ | 80 | 1 | 74 | 74(0) |
| | | | 24 | 80 | 80(0) |
| | $Me_2Ph$ | 80 | 1 | 100 | 75(25) |
| | $Me_2(OSiMe_3)$ | 80 | 1 | 98 | 84(14) |
| | | | 24 | 100 | 85(15) |
| | $Me(OSiMe_3)_2$ | 80 | 1 | 100 | 86(13) |
| C8 | $Et_3$ | 80 | 1 | 28 | 27(1) |
| | | | 24 | 35 | 32(3) |
| | $Me_2Ph$ | 80 | 1 | 75 | 75(0) |
| | | | 24 | 80 | 80(0) |
| | $Me_2(OSiMe_3)$ | 80 | 1 | 42 | 42(0) |
| | | | 24 | 56 | 56(0) |
| | $Me(OSiMe_3)_2$ | 80 | 1 | 88 | 76(12) |
| | | | 24 | 94 | 80(14) |
| C9 | $Et_3$ | 80 | 1 | 90 | 90(0) |
| | | | 24 | 100 | 100(0) |
| | $Me_2Ph$ | 80 | 1 | 60 | 60(0) |
| | | | 24 | 60 | 60(0) |
| | $Me_2(OSiMe_3)$ | 80 | 1 | 63 | 63(0) |
| | | | 24 | 100 | 100(0) |
| | $Me(OSiMe_3)_2$ | 80 | 1 | 56 | 56(0) |
| | | | 24 | 78 | 78(0) |
| C2 | $Et_3$ | 80 | 1 | 26 | 26(0) |
| | | | 24 | 58 | 58(0) |
| | $Me_2Ph$ | 80 | 1 | 12 | 12(0) |
| | | | 24 | 30 | 30(0) |
| | $Me_2(OSiMe_3)$ | 80 | 1 | 64 | 53(11) |
| | | | 24 | 84 | 74(10) |

TABLE 15-3-continued

| Catalyst | $R_3$ | Temp. [° C.] | Time [hours] | Conversion of Si—H [%] | Yield A(B) [%] |
|---|---|---|---|---|---|
| | $Me(OSiMe_3)_2$ | 80 | 1 | 41 | 41(0) |
| | | | 24 | 100 | 100(0) |

Example 16

Application of Iron(0) Complexes in Macromolecular Systems

Samples were prepared by mixing a catalyst prepared by one of the examples above as ingredient (A), a vinyl functional polyorganosiloxane as ingredient (B), and a polyorganosiloxane having silicon bonded hydrogen atoms as ingredient (C). The resulting mixture was cured for a period time at room temperature or with heating, as shown in Tables 16 to 21 below. The amounts of the ingredients in Tables 16 to 21 are mole ratios. A '-' in one of the Tables denotes that a value was not measured under the conditions specified because the sample cured too quickly.

VMS-T11 was a homomethylvinylsiloxane of formula $Me_3SiO(SiMeViO)_wOSiMe_3$ viscosity 7-15 cSt and subscript w has a value ranging from 9 to 16. VDT-431 is a copolymer of formula $Me_3SiO(SiMe_2O)_x(SiMeViO)_yOSiMe_3$ where subscripts x and y were such that the copolymer contained 4 to 5 mol % vinylmethylsiloxane and had a viscosity of 800 to 1200 cSt. HMS-992 was Si—H containing homopolymer of formula $Me_3SiO(SiMeHO)_zOSiMe_3$ having a viscosity of 24 to 30 cSt and subscript z with a value of 27 to 33. DMS-V22 was a vinyl endblocked polymer of formula $ViMe_2SiO(SiMe_2O)_{zz}OSiMe_2Vi$ containing 0.4 to 0.6 Wt % Vinyl and having viscosity of 200 cSt with subscript zz=125. Each of these ingredients was purchased from Gelest, Inc.

TABLE 16

Preliminary curing tests of VMS-T11 and VDT-431 by H-polysiloxane HMS992.

| Catalyst | Siloxanes mixture | Curing time at r.t. | Curing time at 120° C. | Curing time at 150° C. |
|---|---|---|---|---|
| C1 | | $[Fe] = 10^{-2}$ | | |
| | A | + (on mix.) | — | — |
| | B | + (on mix.) | — | — |
| | | $[Fe] = 10^{-3}$ | | |
| | A | — | 3 min | 1.5 min |
| | B | — | 4 min | 1 min |
| C12 | | $[Fe] = 10^{-2}$ | | |
| | A | + (on mix.) | — | — |
| | B | + (on mix.) | — | — |
| | | $[Fe] = 10^{-3}$ | | |
| | A | — | 4 min | 1 min |
| | B | — | 3.5 min | 1 min |

A - [Vi-homopolymer (VMS-T11)]:[crosslinker HMS-992] = $[CH_2{=}CHSi]:[H—Si]$ = 10:1
B - [co-polymer (VDT-431)]:[cross-linker HMS-992] = $[CH_2{=}CHSi]:[H—Si]$ = 10:1
Vi-homopolymer - MW ≈ 2500 g/mol (VMS-T11)
co-polymer - 4 to 5 mol % ViSi (VDT-431)
cross-linker - 1% Si—H (HMS992)

TABLE 17

Curing of DMS-V22 by HMS-992

| Catalyst | Siloxanes mixture | Curing time at r.t. | Curing time at 150° C. |
|---|---|---|---|
| C1 | | $[Fe] = 10^{-2}$ | |
| | A | — | 30 min (no curing) |
| | B | — | 30 min (no curing) |
| C12 | | $[Fe] = 10^{-2}$ | |
| | A | — | 30 min (no curing) |
| | B | — | 30 min (no curing) |

A - [DMS-V22)]:[HMS-992] = 1:1.9;
B - [DMS-V22)]:[HMS-992] = 2:1

TABLE 18

Catalytic activity of iron(0) complexes in curing process of silicon fluids

| Catalyst | Siloxane composition | Curing time [min.] at 120° C. | at 150° C. | at 170° C. |
|---|---|---|---|---|
| C1 | | $[Fe] = 10^{-2}$ | | |
| | C | no curing | 13 | 4 |
| | D | no curing | 23 | 9 |
| C3 | | $[Fe] = 10^{-2}$ | | |
| | C | no curing | 1 min. 25 s. | 1 min. 10 s. |
| | D | no curing | 2 min. 30 s. | 9 min. |
| | E | no curing | no curing | 28 min. 10 s. |
| | | $[Fe] = 10^{-3}$ | | |
| | C | no curing | 1 min. 13 s. | 2 min. |
| | D | no curing | 5 min. 30 s. | 6 min. 20 s. |
| | E | no curing | no curing | no curing |
| **Catalyst** | **Siloxane composition** | **Curing time [min.]** | | |
| C4 | | $[Fe] = 10^{-2}$ | | |
| | C | no curing | 2 min. | 1 min. 30 s. |
| | D | no curing | 4 min. | 2 min. 10 s. |
| | E | no curing | no curing | 19 min. 30 s. |
| | | $[Fe] = 10^{-3}$ | | |
| | C | no curing | 2 min. 15 s. | 3 min. |
| | D | no curing | 5 min. 50 s. | 13 min. 10 s. |
| | E | no curing | no curing | no curing |

C - [DMS-V22]:[cross-linker (HMS-992)] = $[CH_2{=}CHSi]:[H—Si]$ = 1:10
D - [DMS-V22]:[cross-linker (HMS-992)] = $[CH_2{=}CHSi]:[H—Si]$ = 1:5
E - [DMS-V22]:[cross-linker (HMS-992)] = $[CH_2{=}CHSi]:[H—Si]$ = 1:4
cross-linker - 1.64% Si—H (HMS-992)

TABLE 19

Pot-life and curing time at elevated temperature after 20 days.

| Catalyst | Siloxane composition | Curing time [min.] at 150° C. | at 170° C. | Pot life [days] |
|---|---|---|---|---|
| C3 | | $[Fe] = 10^{-2}$ | | |
| | C | 6 min. 40 s. | 1 min. 50 s. | 20 |
| | D | 43 min. 10 s. | 8 min. 20 s. | 20 |
| | E | — | 21 min. | 20 |
| | | $[Fe] = 10^{-3}$ | | |
| | C | 8 min. 40 s. | 3 min. | 20 |
| | D | 44 min. 20 s. | 11 min. 20 s. | 20 |
| | E | — | 38 min. 20 s. | 20 |
| C4 | | $[Fe] = 10^{-2}$ | | |
| | C | 6 min. | 3 min. 50 s. | 20 |
| | D | — | 9 min. 20 s. | 20 |
| | E | — | 28 min. | 20 |
| | | $[Fe] = 10^{-3}$ | | |
| | C | 11 min. 10 s. | 4 min. | 20 |
| | D | — | 10 min. 20 s. | 20 |
| | E | — | | 20 |
| C1 | | $[Fe] = 10^{-2}$ | | |
| | C | 5 min. 15 s. | 2 min. 50 s. | 50 |
| | D | 1 hour 5 min. | 13 min. | 50 |
| | | $[Fe] = 2 * 10^{-3}$ | | |
| | C | 10 min. | 2 min. | 50 |
| | D | 45 min. | 11 min. | 50 |

C - [DMS-V22]:[cross-linker (HMS-992)] = [$CH_2$═CHSi]:[H—Si] = 1:10
D - [DMS-V22]:[cross-linker (HMS-992)] = [$CH_2$═CHSi]:[H—Si] = 1:5
cross-linker - 1.64% Si—H (HMS-992)
E - [DMS-V22]:[cross-linker (HMS-992)] = [$CH_2$═CHSi]:[H—Si] = 1:4
cross-linker - 1.64% Si—H (HMS-992)

TABLE 20

DSC analysis

| Catalyst, [Fe] | Silicone composition | DSC Analysis Average Peak temp. (° C.) | Average Enthalpy of Reaction (J/g) |
|---|---|---|---|
| C1, $10^{-2}$ | C | 220.0 | 5.05 |
| C12, $10^{-2}$ | C | 228.7 | 17.54 |
| C1, $10^{-2}$ | D | — | — |
| C12, $10^{-2}$ | D | 264.6 | 7.88 |
| C1, $10^{-2}$ | G | 209.9 | 36.03 |
| C1, $10^{-3}$ | G | 114.5 | 1.72 |
| | | 208.4 | 6.03 |
| | | 272.8 | 6.66 |
| C12, $10^{-3}$ | G | 240.4 | 12.85 |
| C1, $10^{-2}$ | H | 207.0 | 25.05 |
| C1, $10^{-3}$ | H | 212.4 | 5.19 |
| C12, $10^{-3}$ | H | 207.1 | 9.77 |
| | | 255.5 | 4.12 |

Measurement conditions: range 30-300° C., rate 10° C./min, helium, calibrated with indium.
C - [HSi (HMS-992)]:[ViSi (DMS-V22)] = 10:1
D - [HSi (HMS-992)]:[ViSi (DMS-V22)] = 5:1
G - [His (HMS-992)]:[ViSi (VMS-T11)] = 1:10, HSi = 1 mol % of SiH
H - [HSi (HMS-992)]:[ViSi (VDT-431) = 1:10, HSi = 1 mol % of SiH

TABLE 21

| Catalyst | Siloxane composition | Curing time [min.] at 150° C. | at 170° C. |
|---|---|---|---|
| C7 | | $[Fe] = 10^{-2}$ | |
| | C | 50 s | 35 s |
| | D | 3 min 30 s | 1 min 20 s |
| | | $[Fe] = 10^{-3}$ | |
| | C | 1 min 35 s | 50 s |
| | D | 6 min 45 s | 2 min 35 s |
| C8 | | $[Fe] = 10^{-2}$ | |
| | C | 1 min 35 s | 47 s |
| | D | 5 min 10 s | 2 min |
| | | $[Fe] = 10^{-3}$ | |
| | C | 1 min 50 s | 1 min |
| | D | 5 min 45 s | 2 min 35 s |
| C2 | | $[Fe] = 10^{-2}$ | |
| | C | 1 min 50 s | 45 s |
| | D | 4 min 10 s | 2 min 30 s |
| | | $[Fe] = 10^{-3}$ | |
| | C | 3 min 20 s | 1 min 15 s |
| | D | 8 min 40 s | 2 min 40 s |

C - [DMS-V22]:[cross-linker (HMS-992)] = [$CH_2$═CHSi]:[H—Si] = 1:10
D - [DMS-V22]:[cross-linker (HMS-992)] = [$CH_2$═CHSi]:[H—Si] = 1:5
cross-linker - 1.64% Si—H (HMS-992)

The invention claimed is:

1. A composition comprising: either ingredients comprising (A) a catalytically active reaction product of i) an iron carbonyl compound having general formula (i): $Fe_a(CO)_b$, where subscript a is an integer with a value ranging from 1 to 3, subscript b is an integer with a value ranging from 5 to 12; and ii) a silicon containing ligand that coordinates with Fe, where the silicon containing ligand has, per molecule, at least one atom of Si and at least one aliphatically unsaturated group; and (B) an aliphatically unsaturated compound having an average, per molecule, of one or more aliphatically unsaturated organic groups capable of undergoing hydrosilylation reaction; and optionally (C) an SiH functional compound having an average, per molecule, of one or more silicon bonded hydrogen atoms; which is distinct from ingredients (A) and (B);

with the proviso that when ingredient (B) lacks a silicon bonded hydrogen atom, then the composition includes ingredient (C); or ingredients comprising (A) a catalytically active reaction product of i) an iron carbonyl compound having general formula (i): $Fe_a(CO)_b$, where subscript a is an integer with a value ranging from 1 to 3, subscript b is an integer with a value ranging from 5 to 12; and ii) a polyorganosiloxane ligand that coordinates with Fe, where the ligand has, per molecule, at least one aliphatically unsaturated group, and where the ligand is present in a molar excess based on the molar amount of ingredient i); and optionally (C) an SiH functional compound having an average, per molecule, of one or more silicon bonded hydrogen atoms; which is distinct from ingredient (A) and ingredient ii);

with the proviso that when ingredient ii) lacks a silicon bonded hydrogen atom, then the composition includes ingredient (C).

2. The composition of claim 1, where the composition further comprises one or more additional ingredients, which are distinct from ingredients (A), (B), and (C), and which are selected from the group consisting of (D) a spacer; (E) an extender, a plasticizer, or a combination thereof; (F) a filler; (G) a filler treating agent; (H) a biocide; (I) a stabilizer, (J) a flame retardant; (K) a surface modifier; (L) a chain lengthener; (M) an endblocker; (N) a flux agent; (O) an anti-aging additive; (P) a pigment; (Q) an acid acceptor (R) a rheological additive; (S) a vehicle; (T) a surfactant; (U) a corrosion inhibitor; and a combination thereof.

3. A method comprising: 1) reacting a composition comprising (A) a catalytically active reaction product of i) an iron carbonyl compound having general formula (i): $Fe_a(CO)_b$, where subscript a is an integer with a value ranging from 1 to 2, subscript b is an integer with a value ranging from 5 to 12; and ii) a silicon containing ligand that coordinates with Fe, where the silicon containing ligand has, per molecule, at least one atom of Si and at least one aliphatically unsaturated group; and (B) an aliphatically unsaturated compound having an average, per molecule, of one or more aliphatically unsaturated organic groups capable of undergoing hydrosilylation reaction; and optionally (C) an SiH functional compound having an average, per molecule, of one or more silicon bonded hydrogen atoms; which is distinct from ingredients (A) and (B);

with the proviso that when ingredient (B) lacks a silicon bonded hydrogen atom, then the composition includes ingredient (C).

4. The method of claim 3, further comprising irradiating the iron carbonyl compound and the ligand to form the catalytically active reaction product of ingredient (A) before step 1).

5. The method of claim 4, further comprising removing a by-product from the catalytically active reaction product to yield an Fe-ligand complex free of the by-product before step 1).

6. A method for making the composition of claim 1, comprising: mixing ingredients comprising ingredient (A), ingredient (B), and optionally ingredient (C) so as to make the composition.

7. A reaction product prepared by the method of claim 3.

8. The reaction product of claim 7, where the reaction product has a form selected from a silane, a gum, a gel, a rubber, and a resin.

9. A method comprising: either a step comprising 1) exposing to UV radiation, ingredients comprising:

i) an iron carbonyl compound having general formula (i): $Fe_a(CO)_b$, where subscript a is an integer with a value ranging from 1 to 3, subscript b is an integer with a value ranging from 5 to 12; and ii) a silicon containing ligand that coordinates with Fe, where the silicon containing ligand has, per molecule, at least one atom of Si and at least one aliphatically unsaturated group; or a step comprising 1) exposing to UV radiation, ingredients comprising i) an iron carbonyl compound having general formula (i): $Fe_a(CO)_b$, where subscript a is an integer with a value ranging from 1 to 3, subscript b is an integer with a value ranging from 5 to 12; and ii) a polyorganosiloxane ligand that coordinates with Fe, where the ligand has, per molecule, at least one aliphatically unsaturated group and where the ligand is present in a molar excess based on the molar amount of ingredient i); and optionally (C) an SiH functional compound having an average, per molecule, of one or more silicon bonded hydrogen atoms; which is distinct from ingredient (A) and ingredient ii);

with the proviso that when ingredient ii) lacks a silicon bonded hydrogen atom, then the composition includes ingredient (C).

10. The method of claim 9, where ingredient i) is selected from the group consisting of: iron(0)pentacarbonyl and diironnonacarbonyl.

11. The method of claim 9, where the ligand comprises unit formula:

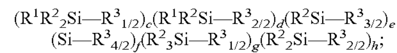

$$(R^1R^2{}_2Si—R^3{}_{1/2})_c(R^1R^2Si—R^3{}_{2/2})_d(R^2Si—R^3{}_{3/2})_e(Si—R^3{}_{4/2})_f(R^2{}_3Si—R^3{}_{1/2})_g(R^2{}_2Si—R^3{}_{2/2})_h;$$

where subscript c is 0 or more; subscript d is 0 or more; subscript e is 0 or more; subscript f is 0 or more; with the proviso that (c+d+e+f)>0; subscript g is 0 or more; subscript h is 0 or more; each $R^1$ is independently an alkynyl group or an alkenyl group; each $R^2$ is independently an alkyl group, a cycloalkyl group, or an aryl group; and each $R^3$ is an oxygen atom or an amino group of formula ═NH.

12. The method of claim 11, where the ligand is a silane of formula (ii): $R^1{}_iSiR^2{}_{(4-i)}$, where each $R^1$ is Vi, each $R^2$ is Me, and subscript i is 2, 3, or 4.

13. The method of claim 11, where the ligand is a cyclic organosilicon compound of formula (iii): $(R^1R^2Si—R^3)_j$, where each $R^1$ is Vi, each $R^2$ is Me, each $R^3$ is O or ═NH, and subscript j is an integer with a value of 3 to 5.

14. The method of claim 13, where the ligand is a linear organosilicon compound of formula (iv): $(R^1{}_kR^2{}_{2-k}Si—R^3)—(R^1R^2Si—R^3)_m(R^2{}_2Si—R^3{}_{2/2})_n—(SiR^1{}_kR^2{}_{2-k})$ where each $R^1$ is Vi, each $R^2$ is Me, each $R^3$ is O or ═NH, subscript m is 1 or more, subscript n is 0 or more, and subscript k is 0 or 1.

15. The method of claim 11, where the the ligand is a linear polyorganosiloxane of formula: $(R^1{}_kR^2{}_{2-k}Si—O)—(R^1R^2Si—O)_m(R^2{}_2Si—O_{2/2})_n—(SiR^1{}_kR^2{}_{2-k})$, where each $R^1$ is Vi, each $R^2$ is Me, subscript m is 1 or more, subscript n is 0 or more, and subscript k is 0 or 1.

16. The method of claim 11, where the ligand is a branched organosilicon compound of formula (v): $(R^1R^2{}_2Si—R^3{}_{1/2})_3(R^2Si—R^3{}_{3/2})$, where each $R^1$ is Vi, each $R^2$ is Me, and each $R^3$ is O.

17. The method of claim 9, where step 1) is performed under an inert atmosphere for 2 hours to 3 hours.

* * * * *